US006388169B1

(12) United States Patent
Mahajan et al.

(10) Patent No.: US 6,388,169 B1
(45) Date of Patent: May 14, 2002

(54) MAIZE ORTHOLOGUES OF BACTERIAL RECA PROTEINS

(75) Inventors: Pramod B. Mahajan, Urbandale; Jinrui Shi, Johnston; Christopher Baszczynski, Urbandale, all of IA (US); John McElver, Durham, NC (US); Benjamin Bowen, Hayward, CA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/310,363

(22) Filed: May 12, 1999

Related U.S. Application Data
(60) Provisional application No. 60/099,765, filed on Sep. 10, 1998, provisional application No. 60/096,492, filed on Aug. 14, 1998, and provisional application No. 60/088,529, filed on Jun. 8, 1998.

(51) Int. Cl.$^7$ .................. C12N 15/09; C12N 15/29; C12N 15/82; A01H 5/00
(52) U.S. Cl. .................. 800/278; 800/286; 800/295; 800/298; 800/320.1; 800/320; 800/320.2; 800/320.3; 800/306; 800/312; 800/314; 800/322; 435/69.1; 435/419; 435/468; 435/320.1; 536/23.2; 536/23.6; 536/24.1; 536/24.5
(58) Field of Search .................. 800/278, 286, 800/320, 320.1, 320.3, 320.2, 306, 312, 314, 322, 295, 298; 435/69.1, 320.1, 468, 419; 536/23.2, 23.6, 24.1, 24.5

(56) References Cited

U.S. PATENT DOCUMENTS
5,674,992 A 10/1997 Jagendorft et al. ........ 536/23.6

FOREIGN PATENT DOCUMENTS
| WO | WO 87/01730 | 3/1987 |
| WO | WO 93/22443 | 11/1993 |
| WO | WO 97/08331 | 3/1997 |

OTHER PUBLICATIONS

Cerutti et al. Proc Natl. Acad. Sci. USA, vol. 89, pp. 8068–8072, 1992.*
Lapointe et al. Biochem Cell Biol. vol. 75, pp. 435–443, Jul. 1997.*
Smith et al. Nature, vol. 334, pp. 724–726, Aug. 1988.*
Chory et al. Plant Physiol. vol. 104, pp. 339–347, 1994.*
Sullivan et al. The Journal of Biological Chemistry, vol. 266, No. 35, pp. 23878–23885, Dec. 1991.*
Cerutti et al. Accession No. M98039, deposited, Apr. 1993.*
Briza et al. Biologia Plantarum, vol. 35, No. 1, pp. 125–129, 1993.*
Lazar et al. Molecular and Cellular Biology, vol. 8, No. 3, pp. 1247–1252, 1988.*
Burgess et al. The Journal of Cell Biology, vol. 111, pp. 2129–2138, 1990.*
Broun et al. Science, vol. 282, pp. 131–133, Nov. 1998.*
Bork et al. Genome Research, vol. 10, pp. 398–400, 2000.*
Reiss et al., "Targeting of a functional *Escherichia coli* RecA protein to the nucleus of plant cells", *Mol Gen Genet*, 253:695–702 (1997).
Binet, N.M., et al., EMBL Accession No. L15229, XP 002113811, "*Arabidopsis thaliana* nuclear–encoded chloroplast DNA repair protein (homologue of *E. coli* recA) gene complete cds."
Binet, N.M., et al., *Plant Gene Reg.*, 103: 673–674, "Genomic nucleotide sequence of a gene from *Arabidopsis thaliana* encoding a protein homolog of *Escherichia coli* RecA".
Dunkin, S.M., et al., EMBL Accession No. UO1959, XP 002113835, "*Rickettsia prowazekii* Madrid E RecA protein (recA) gene, complete cds".
Fyfe, J.A.M., et al., 1990 *Gene*, 93: 151–156, "Nucleotide sequence and expression in *Escherichia coli* of the recA gene of *Neisseria gonorrhoeae*".
Martin, B., et al., EMBL Accession No. Z17307, XP 002113844, "*S. pneumoniae* recA gene encoding RecA".
Sasaki, T., et al., EMBL Accession No. D23629, XP 002113845, "Rice cDNA, partial sequence (C3120_A)".
Wardham, H., et al., 1992, *Gene*, 121: 133–136, "Molecular analysis of the recA gene of *Agrobacterim tumefaciens* C58".
Walbot, V., EMBL Accession No. AI615162, XP 002113837, "486089G04.x1 486—leaf primordia cDNA library from Hake lab *Zea mays* cDNA, mRNA sequence".
Sasaki, T., et al., EMBL Accession No. C98395, XP 002113852. "*Oryza sativa* cDNA, partial sequence (C3120_5A)".
Walbot, V., et al., EMBL Accession No. AI629961, XP 002113857, "486042F11.x2 486—leaf primordia cDNA library from Hake lab *Zea mays* cDNA, mRNA sequence".
Reiss, B., et al., *Proc. Natl. Acad. Sci.* USA, 93: 3094–3098, "RecA protein stimulates homologous recombination in plants".
Clark, A.J. and Margulies, A.D., 1965, *Proc. Natl. Acad. Sci. USA*, 53: 451–459, "Isolation and Characterization of Recombination–Deficient Mutants of *Escherichia COLI K12*"".
Clark, A.J., 1973, *Annu. Rev. Genet.*, 7: 67–86, "Recombination Deficient Mutants of *E. Coli* Other Bacteria".

(List continued on next page.)

*Primary Examiner*—Phuong T. Bui
*Assistant Examiner*—Medina A. Ibrahim
(74) *Attorney, Agent, or Firm*—Pioneer Hi-Bred International, Inc.

(57) ABSTRACT

The present invention provides methods and compositions relating to altering RecA content and/or composition of plants. The invention provides isolated nucleic acids and their encoded proteins that are homologous to bacterial RecA genes. The invention further provides recombinant expression cassettes, host cells, transgenic plants, and antibody compositions. The plant recA polynucleotides and their cognate products are useful for gene targeting in maize and other plant species and for use as a molecular marker.

21 Claims, No Drawings

OTHER PUBLICATIONS

Cox, M.M. and Lehman, I.R., 1987, *Annu. Rev. Biochem.,* 56: 229–262, "Enzymes of General Recombination".

Cerutti, et al., 1992, *Proc. Natl. Acad. Sci. USA,* 89: 8068–8072, "A homolog of *Escherichia coli* RecA protein in plastids of higher plants".

Shinohara, et al., 1993, *Nature Genet.,* 4: 239–243, "Cloning of human, mouse fission yeast recombination genes homologous to RAD51 and recA".

Yoshimura, et al., 1993, *Nucleic Acid Res.,* 21: 1665, "Cloning and sequence of the human RecA–like gene cDNA".

Kowalczykowski, et al., 1994, *Annu. Rev. Biochem.,* 63: 991–1043, "Homologous Pairing and DNA Strand–Exchange Proteins".

Kowalczykowski, et al., 1994, *Microbio Rev.,* 58:401–465, "Biochemistry of Homologous Recombination in *Escherichia coli*".

Reiss, et al., 1999, Keystone Symposia: Molecular Mechanisms in DNA Replication and Recombination, C2: 59, "Bacterial RecA affects homologous recombination and foreign DNA integration in plants".

Scherbakova, et al., 1999, Keystone Symposia: Molecular Mechanisms in DNA Replication and Recombination, C2: 60, "Bacterial RecA protein stimulates homologous recombination in mammalian cells".

* cited by examiner

MAIZE ORTHOLOGUES OF BACTERIAL RECA PROTEINS

CROSS-REFERENCE TO RELATED APPLICATIONS

This application claims the benefit of U.S. Application Ser. No. 60/099,765 filed Sep. 10, 1998, U.S. Application Ser. No. 60/096,492 filed Aug. 14, 1998, and U.S. Application Ser. No. 60/088,529 filed Jun. 8, 1998, all of which are herein incorporated by reference.

TECHNICAL FIELD

The present invention relates generally to plant molecular biology. More specifically, it relates to nucleic acids and methods for modulating their expression in plants.

BACKGROUND OF THE INVENTION

Transgenic plant product development by conventional transformation and breeding efforts is a slow and unpredictable process. Gene targeting systems can overcome problems with expression variability, the unpredictable impact of random gene insertion on agronomic performance, and the large number of experiments that need to be conducted. Such systems can also provide approaches to manipulating endogeneous genes. Of course, a targeting system requires the ability to focus the recombination process to favor recovery of desired targeting events.

The bacterial recA gene and the cognate product RecA protein have been a subject of intense research for the past two decades. The recA gene and RecA protein play a crucial role in genetic recombination (Clark, A. J. and Margulies, A. D. (1965) Proc. Natl. Acad. Sci. USA 53, 451–459; Clark A. J. (1973) Annu. Rev. Genet. 7, 67–86; Cox, M. M. and Lehman, I. R. (1987) Annu. Rev. Biochem. 56, 229–262). Homologues of RecA have been reported in many prokaryotes (Kowalczykowaski S.C. and Eggleston, A. K. (1994) Annu. Rev. Biochem. 63, 991–1043; Kowalczykowaski, et al. (1994) Microbiol. Rev. (1994) 58, 401–465) as well as eukaryotes including humans (reviewed in Kowalczykowaski, et al. (1994) Annu. Rev. Biochem. 63, 991–1043; Kowalczykowaski, et al. (1994) Microbiol. Rev. 58: 401–465; Shinohara, et al. (1993) Nature Genet. 4: 239–243; Yoshimura, et al. (1993) Nucleic Acid Res. 21: 1665). In plants, a RecA homologue from *Arabidopsis thaliana* has been reported (Cerutti, et a., *Proc Natl Acad Sci USA* 89:8068–8072). No maize RecA homologues have been previously identified.

The eukaryotic homologues of RecA are typically grouped with the yeast Rad51 protein. The *E.coli* RecA and yeast Rad51 proteins and their respective genes have been investigated extensively and serve as prokaryotic and eukaryotic models for further studies (Kowalczykowaski, et al. (1994) Annu. Rev. Biochem. 63, 991–1043; Kowalczykowaski, et al. (1994) Microbiol. Rev. 58: 401–465; Shinohara, et al. (1993) Nature Genet. 4: 239–243; Yoshimura, et al. (1993) Nucleic Acid Res. 21: 1665).

It is well known that RecA binds single stranded DNA and promotes pairing and strand exchange between homologous DNA molecules. Reports of the use of bacterial RecA in association with DNA sequences to manipulate homologous target DNA, including improvement of the efficiency of gene targeting in non-plant systems, have been published (see, e.g., PCT published Patent Application Nos. WO 87/01730 and WO 93/22443).

The bacterial RecA as well as the yeast and human homologues also exhibit DNA dependent ATPase activity. However, the precise mechanism(s) by which RecA recognizes homology within a duplex DNA molecule remains unknown. The role of the Rad51 group of proteins in DNA recombination of higher eukaryotes is also ill defined.

To date, work with recombinase enzymes in plants has been very limited. Accordingly, there is an ongoing need for the identification and characterization of the functional activities of recombinase enzymes which may offer improved and expanded methods for use in plant systems, particularly agriculturally important crop species such as maize.

SUMMARY OF THE INVENTION

Generally, it is the object of the present invention to provide nucleic acids and proteins relating to genetic recombination. It is an object of the present invention to provide antigenic fragments of the proteins of the present invention. It is an object of the present invention to provide transgenic plants comprising the nucleic acids of the present invention. Additionally, it is an object of the present invention to provide methods for modulating, in a transgenic plant, the expression of the nucleic acids of the present invention.

Therefore, in one aspect, the present invention relates to an isolated nucleic acid comprising a member selected from the group consisting of (a) a polynucleotide having at least 60% identity to a polynucleotide encoding a polypeptide selected from the group consisting of SEQ ID NOS: 2, 4, 6, and 8 wherein the polypeptide when presented as an immunogen elicits the production of an antibody which is specifically reactive to the polypeptide; (b) a polynucleotide which is complementary to the polynucleotide of (a); and (c) a polynucleotide comprising at least 25 contiguous nucleotides from a polynucleotide of (a) or (b). In some embodiments, the polynucleotide has a sequence selected from the group consisting of SEQ ID NOS: 1, 3, 5, and 7. The isolated nucleic acid can be DNA.

In another aspect, the present invention relates to recombinant expression cassettes, comprising a nucleic acid as described, supra, operably linked to a promoter. In some embodiments, the nucleic acid is operably linked in antisense orientation to the promoter.

In another aspect, the present invention is directed to a host cell transfected with the recombinant expression cassette as described, supra. In some embodiments, the host cell is a sorghum (*Sorghum bicolor*), maize (*Zea mays*), rice (*Oryza sativa*), or wheat (*Triticum aestivum*) cell.

In a further aspect, the present invention relates to an isolated protein comprising a polypeptide of at least 10 contiguous amino acids encoded by the isolated nucleic acid referred to, supra. In some embodiments, the polypeptide has a sequence selected from the group consisting of SEQ ID NOS: 2, 4, 6 and 8.

In another aspect, the present invention relates to an isolated nucleic acid comprising a polynucleotide of at least 25 nucleotides in length which selectively hybridizes under stringent conditions to a nucleic acid selected from the group consisting of SEQ ID NOS: 1, 3, 5, and 7 or a complement thereof. In some embodiments, the isolated nucleic acid is operably linked to a promoter.

In yet another aspect, the present invention relates to an isolated nucleic acid comprising a polynucleotide, the polynucleotide having at least 80% sequence identity to an identical length of a nucleic acid selected from the group consisting of SEQ ID NOS: 1, 3, 5, and 7 or a complement thereof.

In another aspect, the present invention relates to an isolated nucleic acid comprising a polynucleotide having a sequence of a nucleic acid amplified from a Zea mays nucleic acid library using the primers designed from the 5' and 3' end of the polynucleotide selected from the group consisting of SEQ ID NOS: 1, 3, 5, and 7 or a complement thereof. In some embodiments, the nucleic acid library is a cDNA library.

In another aspect, the present invention relates to a recombinant expression cassette comprising a nucleic acid amplified from a library as referred to supra, wherein the nucleic acid is operably linked to a promoter. In some embodiments, the present invention relates to a host cell transfected with this recombinant expression cassette In some embodiments, the present invention relates to a protein of the present invention which is produced from this host cell.

In an additional aspect, the present invention is directed to an isolated nucleic acid comprising a polynucleotide encoding a polypeptide wherein: (a) the polypeptide comprises at least 10 contiguous amino acid residues from a first polypeptide selected from the group consisting of SEQ ID NOS: 2, 4, 6, and 8 wherein said polypeptide, when presented as an immunogen, elicits the production of an antibody which specifically binds to said first polypeptide; (b) the polypeptide does not bind to antisera raised against the first polypeptide which has been fully immunosorbed with the first polypeptide; (c) the polypeptide has a molecular weight in non-glycosylated form within 10% of the first polypeptide.

In a further aspect, the present invention relates to a heterologous promoter operably linked to a non-isolated polynucleotide of the present invention, wherein the polypeptide is encoded by a nucleic acid amplified from a nucleic acid library.

In yet another aspect, the present invention relates to a transgenic plant comprising a recombinant expression cassette comprising a plant promoter operably linked to any of the isolated nucleic acids of the present invention. In some embodiments, the transgenic plant is Zea mays. The present invention also provides transgenic seed from the transgenic plant.

In a further aspect, the present invention relates to a method of modulating expression of the polynucleotides encoding the proteins of the present invention in a plant, comprising the steps of (a) transforming a plant cell with a recombinant expression cassette comprising a polynucleotide of the present invention operably linked to a promoter; (b) growing the plant cell under plant growing conditions; and (c) inducing expression of the polynucleotide for a time sufficient to modulate expression of the genes in the plant. In some embodiments, the plant is maize. Expression of the polynucleotides encoding the proteins of the present invention can be increased or decreased relative to a non-transformed control plant.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies comple-mentary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substance capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246: 1275–1281 (1989); and Ward, et al., *Nature* 341: 544–546 (1989); and Vaughan et al., *Nature Biotech.* 14: 309–314 (1996).

As used herein, "antisense orientation" includes reference to a duplex polynucleotide sequence which is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of chromosome which may be measured by reference to the linear segment of DNA which it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also describes every possible silent variation of the nucleic acid. One of ordinary skill will recognize that each codon in a nucleic acid (except AUG, which is ordinarily the only codon for methionine) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
See also, Creighton (1984) Proteins W.H. Freeman and Company.

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC at 60° C.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.* (*USA*), 82: 2306–2309 (1985)), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, catalytically active form of the specified protein. A full-length sequence can be determined by size comparison relative to a control which is a native (non-synthetic) endogenous cellular form of the specified nucleic acid or protein. Methods to determine whether a sequence is full-length are well known in the art including such exemplary techniques as northern or western blots, primer extension, Si protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end.

Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural polynucleotide is from a species different from that from which the structural polynucleotide was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the expression vector. Host cells may be prokaryotic cells such as *E. coli,* or eukaryotic cells such as yeast, insect, amphibian, or mammalian cells. Preferably, host cells are monocotyledonous or dicotyledenous plant cells. A particularly preferred monocotolydenous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, generated to a particular epitope, to bind to that epitope to a detectably greater degree (e.g., at least 2-fold over background) than the antibody binds to substantially all other epitopes in a reaction mixture comprising the particular epitope. Immunologically reactive conditions are dependent upon the format of the antibody binding reaction and typically are those utilized in immunoassay protocols. See Harlow and Lane, *Antibodies, A Laboratory Manual,* Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by non-natural, synthetic (i.e., "manmade") methods performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

The term "non-isolated", as used herein, generally means a nucleic acid or a protein that is found in its naturally occurring environment, e.g. non-heterologous DNA found in the genetic material of the cell. The non-isolated material may be a nucleic acid sequence operably linked to a heterologous nucleic acid sequence. The linking can be accomplished by targeted homologous recombination. See, e.g., In Vivo Homologous Sequence Targeting in Eukaryotic Cells; Zarling et al., PCT/US93/03868.

Unless otherwise stated, the term "RecA nucleic acid" means a nucleic acid comprising a polynucleotide ("RecA polynucleotide") encoding a RecA polypeptide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology,* Vol. 152, Academic Press, Inc., San Diego, Calif. (Berger); *Sambrook et al., Molecular Cloning—A Laboratory Manual,* 2nd ed., Vol. 1–3 (1989); and *Current Protocols in Molecular Biology,* F. M. Ausubel et al., Eds., Current Protocols, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Exemplary modifications are described in most basic texts, such as, *Proteins— Structure and Molecular Properties,* 2nd ed., T. E. Creighton, W. H. Freeman and Company, New York (1993). Many detailed reviews are available on this subject, such as, for example, those provided by Wold, F., Posttranslational Protein Modifications: Perspectives and Prospects, pp. 1–12 in *Posttranslational Covalent Modification of Proteins,* B. C. Johnson, Ed., Academic Press, New York (1983); Seifter et al., *Meth. Enzymol.* 182: 626–646 (1990) and Rattan et al., *Protein Synthesis: Posttranslational Modifications and Aging, Ann. N.Y. Acad Sci.* 663: 48–62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention. In general, as used herein, the term polypeptide encompasses all such modifications, particularly those that are present in polypeptides synthesized by expressing a polynucleotide in a host cell.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such Agrobacterium or Rhizobium. Examples of promoters under developmental control include promoters that preferentially initiate transcription in certain tissues, such as leaves, roots, seeds, fibres, xylem vessels, tracheids, or sclerenchyma. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "RecA polypeptide" refer to one or more amino acid sequences, in glycosylated or non-glycosylated form, involved in the RecA pathway. The term is also inclusive of fragments, variants, homologs, alleles or precursors (e.g., preproproteins or proproteins) thereof. A "RecA protein" comprises a RecA polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, as generated recombinantly or synthetically, with a series of specified nucleic acid elements which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all other analytes lacking the epitope which are present in the sample.

Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, *Antibodies, A Laboratory Manual*, Cold Spring Harbor Publications, New York (1988), for a description of immunoassay formats and conditions that can be used to determine selective reactivity.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Unless otherwise stated, in the present application high stringency is defined as hybridization in 4×SSC, 5× Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m$=81.5° C.+16.6 (log M)+0.41 (%GC)–0.61 (% form)–500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology— Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection or transformation of a host cell and into which can be inserted a polynucleotide. Vectors are often replicons. Expression vectors permit transcription and translation of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity"

(a) As used herein, "reference sequence" is a defined sequence used as a basis for sequence comparison. A reference sequence may be a subset or the entirety of a specified sequence; for example, as a segment of a full-length cDNA or polynucleotide sequence, or the complete cDNA or polynucleotide sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well-known in the art. Optimal alignment of sequences for comparison may be conducted by the local homology algorithm (Best Fit) of Smith and Waterman, *Adv. Appl. Math.* 2: 482 (1981); by the homology alignment algorithm (GAP) of Needleman and Wunsch, *J. Mol. Biol.* 48: 443 (1970); by the search for similarity method (Tfasta and Fasta) of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, California, GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). The preferred program to use for optimal global alignment of multiple sequences is PileUp (Feng and Doolittle, *Journal of Molecular Evolution,* 25:351–360 (1987) which is similar to the method described by Higgins and Sharp, *CABIOS,* 5:151–153 (1989) and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology,* Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389–3402 (1997).

As those of ordinary skill in the art will understand, BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.,* 17:149–163 (1993)) and XNU (Claverie and States, *Comput. Chem.,* 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 60% sequence identity, preferably at least 70%, more preferably at least 80%, even more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acid substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DETAILED DESCRIPTION OF THE INVENTION

Overview

The present invention provides, inter alia, compositions and methods for modulating (i.e., increasing or decreasing) the total levels of proteins of the present invention and/or altering their ratios in plants. Thus, the present invention provides utility in such exemplary applications as gene targeting in maize and other plant species. In particular, the polypeptides of the present invention can be expressed at times, in tissues, and/or in quantities which are uncharacteristic of non-recombinant plants.

The present invention also provides isolated nucleic acid comprising polynucleotides of sufficient length and complementarity to a RecA polynucleotide to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the polynucleotide (e.g., substitutions, deletions, or additions), for monitoring upregulation of expression or changes in enzyme activity in screening assays of compounds, for detection of any number of allelic variants (polymorphisms) of the polynucleotide, or for use as molecular markers in plant breeding programs. The isolated nucleic acids of the present invention can also be used for recombinant expression of RecA polypeptides, or for use as immunogens in the preparation and/or screening of antibodies. The isolated nucleic acids of the present invention can also be employed for use in sense or antisense suppression of one or more RecA polynucleotides in a host cell, tissue, or plant. Attachment of chemical agents which bind, intercalate, cleave and/or crosslink to the isolated nucleic acids of the present invention can also be used to modulate transcription or translation. Further, using a primer specific to an insertion sequence (e.g., transposon) and a primer which specifically hybridizes to an isolated nucleic acid of the present invention, one can use nucleic acid amplification to identify insertion sequence inactivated RecA polynucleotides from a cDNA library prepared from insertion sequence mutagenized plants. Progeny seed from the plants comprising the desired inactivated polynucleotide can be grown to a plant to study the phenotypic changes characteristic of that inactivation. See, *Tools to Determine the Function of Genes,* 1995 Proceedings of the Fiftieth Annual Corn and Sorghum Industry Research Conference, American Seed Trade Association, Washington, D.C., 1995. Additionally, non-translated 5' or 3' regions of the polynucleotides of the present invention can be used to modulate turnover of heterologous mRNAs and/or protein synthesis. Further, the codon preference characteristic of the polynucleotides of the present invention can be employed in heterologous sequences, or altered in homologous or heterologous sequences, to modulate translational level and/or rates.

The present invention also provides isolated proteins comprising polypeptides including an amino acid sequence from the RecA polypeptides (e.g., preproenzyme, proenzyme, or enzymes) as disclosed herein. The present invention also provides proteins comprising at least one epitope from a RecA polypeptide. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, or for purification of RecA polypeptides.

The isolated nucleic acids of the present invention can be used over a broad range of plant types, including species from the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, and Populus.

Nucleic Acids

The present invention provides, inter alia, isolated nucleic acids of RNA, DNA, and analogs and/or chimeras thereof, comprising a RecA polynucleotide encoding such enzymes as recombinases.

The RecA nucleic acids of the present invention comprise an isolated RecA polynucleotides which, are inclusive of:

(a) a polynucleotide encoding a RecA polypeptide of SEQ ID NOS: 2, 4, 6, and 8 and conservatively modified and polymorphic variants thereof;

(b) a polynucleotide which is the product of amplification from a *Zea mays* nucleic acid library using primer pairs from amongst the consecutive pairs, which amplify polynucleotides having substantial identity to polynucleotides from amongst those having SEQ ID NOS: 1, 3, 5 and 7;

(c) a polynucleotide which selectively hybridizes to a polynucleotide of (a) or (b);

(d) a polynucleotide having at least 60% sequence identity with polynucleotides of (a), (b), or (c);

(e) a polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d), or (e); and (g) a polynucleotide comprising at least 15 contiguous nucleotides from a polynucleotide of (a), (b), (c), (d), (e), or (f).

A. Polynucleotides Encoding a Protein of SEQ ID NOS: 2, 4, 6, and 8 or Conservatively Modified or Polymorphic Variants Thereof As indicated in (a), supra, the present invention provides isolated heterologous nucleic acids comprising a RecA polynucleotide, wherein the polynucleotide encodes a RecA polypeptide, disclosed herein in SEQ ID NOS: 2, 4, 6, and 8 or conservatively modified or polymorphic variants thereof. Those of skill in the art will recognize that the degeneracy of the genetic code allows for a plurality of polynucleotides to encode for the identical amino acid sequence. Such "silent variations" can be used, for example, to selectively hybridize and detect allelic variants of polynucleotides of the present invention. Accordingly, the present invention includes polynucleotides of SEQ ID NOS: 1, 3, 5, and 7 and silent variations of polynucleotides encoding a polypeptide of SEQ ID NOS: 2, 4, 6, and 8. The present invention further provides isolated nucleic acids comprising polynucleotides encoding conservatively modified variants of a polypeptide of SEQ ID NOS: 2, 4, 6 and 8. Conservatively modified variants can be used to generate or select antibodies immunoreactive to the non-variant polypeptide. Additionally, the present invention further provides isolated nucleic acids comprising polynucleotides encoding one or more polymorphic (allelic) variants of polypeptides/polynucleotides. Polymorphisms are frequently used to follow segregation of chromosomal regions in, for example, marker assisted selection methods for crop improvement.

B. Polynucleotides Amplified from a *Zea mays* Nucleic Acid Library

As indicated in (b), supra, the present invention provides isolated nucleic acids comprising RecA polynucleotides, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. Generally, a cDNA nucleic acid library will be constructed to comprise a majority of full-length cDNAs. Often, cDNA libraries will be normalized to increase the representation of relatively rare cDNAs. In preferred embodiments, the cDNA library is constructed. In preferred embodiments, the cDNA library is constructed using a full-length cDNA synthesis method. Examples of such methods include Oligo-Capping (Maruyama, K. and Sugano, S. Gene 138: 171–174, 1994), Biotinylated CAP Trapper (Carninci, P., Kvan, C., et al. Genomics 37: 327–336, 1996), and CAP Retention Procedure (Edery, E., Chu, L. L., et al. Molecular and Cellular Biology 15:3363–3371, 1995). cDNA synthesis is preferably catalyzed at 50–55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and Retro-Amp Reverse Transcriptase (Epicentre). Rapidly growing tissues, or rapidly dividing cells are preferably used as mRNA sources.

The present invention also provides subsequences of full-length nucleic acids. Any number of subsequences can be obtained by reference to SEQ ID NOS: 1, 3, 5, and 7 and using primers which selectively amplify, under stringent conditions to: at least two sites to the polynucleotides of the present invention, or to two sites within the nucleic acid which flank and comprise a polynucleotide of the present invention, or to a site within a polynucleotide of the present invention and a site within the nucleic acid which comprises it. A variety of methods for obtaining 5' and/or 3' ends is well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego, 1990), pp. 28–38.); see also, U.S. Pat. No. 5,470,722, and *Current Protocols in Molecular Biology,* Unit 15.6, Ausubel, et al., Eds., Greene Publishing and Wiley-Interscience, New York (1995). Thus, the present invention provides RecA polynucleotides having the sequence of the RecA gene, nuclear transcript, cDNA, or complementary sequences and/or subsequences thereof.

Primer sequences can be obtained by reference to a contiguous subsequence of a polynucleotide of the present invention. Primers are chosen to selectively hybridize, under PCR amplification conditions, to a polynucleotide of the present invention in an amplification mixture comprising a genomic and/or cDNA library from the same species. Generally, the primers are complementary to a subsequence of the amplicon they yield. In some embodiments, the primers will be constructed to anneal at their 5' terminal end's to the codon encoding the carboxy or amino terminal amino acid residue (or the complements thereof) of the polynucleotides of the present invention. The primer length in nucleotides is selected from the group of integers consisting of from at least 15 to 50. Thus, the primers can be at least 15, 18, 20, 25, 30, 40, or 50 nucleotides in length. A non-annealing sequence at the 5'end of the primer (a "tail") can be added, for example, to introduce a cloning site at the terminal ends of the amplicon.

The amplification primers may optionally be elongated in the 3' direction with additional contiguous nucleotides from the polynucleotide sequences, such as SEQ ID NOS: 1, 3, 5, and 7 from which they are derived. The number of nucleotides by which the primers can be elongated is selected from the group of integers consisting of from at least 1 to 25. Thus, for example, the primers can be elongated with an additional 1, 5, 10, or 15 nucleotides. Those of skill will recognize that a lengthened primer sequence can be employed to increase specificity of binding (i.e., annealing) to a target sequence.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog '97, p.354.

C. Polynucleotides which Selectively Hybridize to a Polynucleotide of (A) or (B)

As indicated in (c), supra, the present invention provides isolated nucleic acids comprising RecA polynucleotides, wherein the polynucleotides selectively hybridize, under selective hybridization conditions, to a polynucleotide of paragraphs (A) or (B) as discussed, supra. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or fill-length clones in a deposited library. In some embodiments, the polynucleotides are genomic or cDNA sequences isolated, or otherwise complementary to, a cDNA from a *Zea mays* nucleic acid library. Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having at Least 60% Sequence Identity with the Polynucleotides of (A), (B) or (C)

As indicated in (d), supra, the present invention provides isolated nucleic acids comprising RecA polynucleotides, wherein the polynucleotides have a specified identity at the nucleotide level to a polynucleotide as disclosed above in paragraphs (A), (B), or (C). The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

Optionally, the polynucleotides of this embodiment will share an epitope with a polypeptide encoded by the polynucleotides of (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 96/19256. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), supra, the present invention provides isolated nucleic acids comprising RecA polynucleotides, wherein the polynucleotides encode a protein having a subsequence of contiguous amino acids from a prototype RecA polypeptide. Exemplary prototype RecA polypeptides are provided in SEQ ID NOS: 2, 4, 6, and 8. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as, but not limited to, a polypeptide encoded by the polynucleotide of (b), supra, or exemplary polypeptides of SEQ ID NOS: 2, 4, 6, and 8. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated RecA polypeptides as disclosed herein (e.g., SEQ ID NOS: 2, 4, and 6). Molecular weight can be readily determined by SDS-PAGE under reducing conditions. Preferably, the molecular weight is within 15% of a full length RecA polypeptide, more preferably within 10% or 5%, and most preferably within 3%, 2%, or 1% of a full length RecA polypeptide of the present invention. Molecular weight determination of a protein can be conveniently performed by SDS-PAGE under denaturing conditions.

Optionally, the polynucleotides of this embodiment will encode a protein having a specific activity at least 20%, 30%, 40%, or 50% of the native, endogenous (i.e., non-isolated), full-length RecA polypeptide. Further, the proteins encoded by polynucleotides of this embodiment will optionally have a substantially similar apparent dissociation constant ($K_m$) and/or catalytic activity (i.e., the microscopic rate constant, $k_{cat}$) as the native endogenous, full-length RecA protein. Those of skill in the art will recognize that $k_{cat}/K_m$ value determines the specificity for competing substrates and is often referred to as the specificity constant. Proteins of this embodiment can have a $k_{cat}/K_m$ value at least 10% of the non-isolated full-length RecA polypeptide as determined using the substrate of that polypeptide from the RecA specific pathways, supra. Optionally, the $k_{cat}/K_m$ value will be at least 20%, 30%, 40%, 50%, and most preferably at least 60%, 70%, 80%, 90%, or 95% the $k_{cat}/K_m$ value of the non-isolated, full-length RecA polypeptide. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

As indicated in (f), supra, the present invention provides isolated nucleic acids comprising RecA polynucleotides, wherein the polynucleotides are complementary to the polynucleotides of paragraphs A–E, above. As those of skill in the art will recognize, complementary sequences base-pair throughout the entirety of their length with the polynucleotides of (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides which are Subsequences of the Polynucleotides of (A)–(F)

As indicated in (g), supra, the present invention provides isolated nucleic acids comprising RecA polynucleotides, wherein the polynucleotide comprises at least 15 contiguous bases from the polynucleotides of (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75, or 100 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from I to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived. For example, a subsequence from a polynucleotide encoding a polypeptide having at least one linear epitope in common with a prototype sequence, such as SEQ ID NOS: 2, 4, 6, and 8 may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some A embodiments, the polynucleotides of the present invention will be cloned, amplified, or otherwise constructed from a monocot. In preferred embodiments the monocot is *Zea mays*. Particularly preferred is the use of *Zea mays* tissue.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pOPRSVI CAT, pOP13 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of proteins, followed by precipitation of nucleic acids. Extraction of total RNA from plant cells can be accomplished by a variety of means. Frequently, extraction buffers include a strong detergent such as SDS and an organic deanturant such as guanidinium isothiocyanate, guanidine hydrochloride or phenol. Following total RNA isolation, poly(A)$^+$ mRNA is typically purified from the remainder RNA using oligo(dT) cellulose. Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, first strand cDNA synthesis is initiated from a poly(A)$^+$ mRNA template using a poly(dT) primer or random hexanucleotides. Second, the resultant RNA-DNA hybrid is converted into double stranded cDNA, typically by a combination of RNAse H and DNA polymerase I (or Klenow fragment). Third, the termini of the double stranded cDNA are ligated to adaptors. Ligation of the adaptors will produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as Stratagene or Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Carninci et al., *Genomics*, 37:327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al, *Mol. Cell Biol.*, 15(6):3363–3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res.*, 18(19):5705–5711 (1990); Patanjali et al., *Proc. Natl. Acad. U.S.A.*, 88:1943–1947 (1991); U.S. Pat. Nos. 5,482,685, and 5,637,685. In an exemplary method described by Soares et al., normalization resulted in reduction of the abundance of clones from a range of four orders of magnitude to a narrow range of only 1 order of magnitude. *Proc. Natl. Acad. Sci. USA*, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.*, 16(22):10937 (1988); *Current Protocols in Molecular Biology*, Ausubel, et al., Eds., Greene Publishing and Wiley-Interscience, New York (1995); and, Swaroop et al., *Nucl. Acids Res.*, 19)8):1954 (1991). cDNA subtraction kits are commercially available. See, e.g., PCR-Select (Clontech).

A4. Construction of a Genomic Library

To construct genomic libraries, large segments of genomic DNA are generated by random fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications,* Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques,* 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, supra.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.,* 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/ selective expression), a transcription initiation start site, a ribosome binding site, an RNA processing signal, a transcription termination site, and/or a polyadenylation signal. An example of a preferred expression cassette in a plasmid capable of expressing the RecA polynucleotides in a plant, is the insertion of a RecA polynucleotide between a maize ubiquitin promoter and a potato proteinase inhibitor ("PinII") terminator in a pUC19 plasmid backbone.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens,* the ubiquitin 1 promoter, the Smas promoter, the cinnamyl alcohol dehydrogenase promoter (U.S. Pat. No. 5,683,439), the Nos promoter, the pEmu promoter, the rubisco promoter, ZmDJ1 promoter (Baszczynski et al., *Maydica,* 42:189–201 (1997)), the GRP 1–8 promoter, and other transcription initiation regions from various plant genes known to those of skill. Examples of suitable promoters which may be operably linked to the present RecA coding sequences include the maize ubiquitin promoter and the ZmDJ1 promoter.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter RecA content and/or composition in a desired tissue. Thus, in some embodiments, the nucleic acid construct will comprise a promoter functional in a plant cell, such as in Zea mays, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a RecA polynucleotide so as to control the expression of the polynucleotide. Polynucleotide expression can be modulated under conditions suitable for plant growth so as to alter RecA content and/or composition. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., *The Maize Handbook,* Chapters 114–115, Freeling and Walbot, Eds., Springer, N.Y. (1994); *Corn and Corn Improvement,* $3^{rd}$ edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that do not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5–10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook,* Chapter 114, Freeling and Walbot, Eds., Springer, N.Y., (1994).

In plants, further upstream from the TATA box, at positions –80 to –100, there is typically a promoter element (i.e., the CAAT box) with a series of adenines surrounding the trinucleotide G (or T) N G. J. Messing et al., in *Genetic Engineering in Plants,* Kosage, Meredith and Hollaender, Eds., pp. 221–227 1983. In maize, there is no well conserved CAAT box but there are several short, conserved protein-binding motifs upstream of the TATA box. These include motifs for the transacting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook,* Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. In Enzymol., 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to alter gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci. (USA)* 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Proteins

The isolated proteins of the present invention comprise a polypeptide having at least 10 amino acids encoded by any one of the polynucleotides of the present invention as discussed more fully, supra, or polypeptides which are conservatively modified variants thereof. Exemplary polypeptide sequences are provided in SEQ ID NOS: 2, 4, 6, and 8. The proteins of the present invention or variants thereof can comprise any number of contiguous amino acid residues from a polypeptide of the present invention, wherein that number is selected from the group of integers consisting of from 10 to the number of residues in a full-length RecA polypeptide. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

As those of skill will appreciate, the present invention includes catalytically active polypeptides of the present invention (i.e., enzymes). Catalytically active polypeptides have a specific activity at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention encoded by a polynucleotide of the present invention as described, supra. Exemplary polypeptides include those which are full-length, such as those disclosed in SEQ ID NOS: 2, 4, 6, and 8. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques. The RecA polynucleotide sequences contain the 27 nucleotide or 9 amino acid RecA signature sequence. The conserved consensus pattern would be particularly useful in the production of antibodies.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of *E. coli;* however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus sp.* and *Salmonella* (Palva, et al, *Gene* 22: 229–235 (1983); Mosbach, et al., *Nature* 302: 543–545 (1983)).

B. Expression in Eukaryotes

A variety of eukaryotic expression systems such as yeast, insect cell lines, plant and mammalian cells, are known to those of skill in the art. As explained briefly below, the polynucleotides of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics,* Cold Spring Harbor Laboratory (1982) is a well recognized work describing the various methods available to produce the protein in yeast. Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., *Gene* 8: 17–24 (1979); Broach, et al., *Gene* 8: 121–133 (1979)).

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See Schneider, *J. Embryol Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A. Plant Transformation

A DNA sequence coding for the desired polynucleotide of the present invention, for example a cDNA or a genomic sequence encoding a full length protein, will be used to construct a recombinant expression cassette which can be introduced into the desired plant. The preferred method of transforming into a plant the polynucleotides of the present invention would be via particle bombardment or Agrobacterium-mediated transformation.

Isolated nucleic acid acids of the present invention can be introduced into plants according techniques known in the art. Generally, recombinant expression cassettes as described above and suitable for transformation of plant cells are prepared. Techniques for transforming a wide variety of higher plant species are well known and described in the technical, scientific, and patent literature. See, for example, Weising et al., *Ann. Rev. Genet.* 22: 421–477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

The introduction of DNA constructs using polyethylene glycol precipitation is described in Paszkowski et al., *Embo J.* 3: 2717–2722 (1984). Electroporation techniques are described in Fromm et al., *Proc. Natl. Acad. Sci.* 82: 5824 (1985). Ballistic transformation techniques are described in Klein et al., *Nature* 327: 70–73 (1987). *Agrobacterium tumefaciens*-meditated transformation techniques are well described in the scientific literature. See, for example Horsch et al., *Science* 233: 496–498 (1984), and Fraley et al., *Proc. Natl. Acad. Sci.* 80: 4803 (1983). Although Agrobacterium is useful primarily in dicots, certain monocots can be transformed by Agrobacterium. For instance, Agrobacterium transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, PWJ Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A.rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25: 1353, 1984), (3) the vortexing method (see, e.g., Kindle, *Proc. Natl. Acad. Sci., USA* 87: 1228, (1990).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding genes can be obtained by injection of the DNA into reproductive organs of a plant as described by Pena et al., Nature, 325.:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986). A variety of plant viruses that can be employed as vectors are known in the art and include cauliflower mosaic virus (CaMV), geminivirus, brome mosaic virus, and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology,* Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology.* Vol. 2: *Special Methods in Peptide Synthesis, Part A.;* Merrifield, et al., *J. Am. Chem. Soc.* 85: 2149–2156 (1963), and Stewart et al., *Solid Phase Peptide Synthesis,* 2nd ed, Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including selective precipitation with such substances as ammonium sulfate, column chromatography, immunopurification methods, and others. See, for instance, R. Scopes, *Protein Purification: Principles and Practice,* Springer-Verlag: New York (1982); Deutscher, *Guide to Protein Purification,* Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture,* Macmillilan Publishing Company, New York, pp. 124–176 (1983); and Binding, *Regeneration of Plants, Plant Protoplasts,* CRC Press, Boca Raton, pp. 21–73 (1985).

The regeneration of plants containing the foreign gene introduced by Agrobacterium from leaf explants can be achieved as described by Horsch et al., *Science,* 227:1229–1231 (1985). In this procedure, transformants are grown in the presence of a selection agent and in a medium that induces the regeneration of shoots in the plant species being transformed as described by Fraley et al., *Proc. Natl. Acad. Sci. U.S.A.,* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al, *Ann. Rev. of Plant Phys.* 38: 467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook,* Freeling and Walbot, Eds., Springer, N.Y. (1994); *Corn and Corn Improvement,* $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype, (e.g., altered RecA content or composition).

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selling) a heterozygous transgenic plant that contains a single added heterologous nucleic acid, germinating some of the seed produced and analyzing the resulting plants produced for altered lignification relative to a control plant (i.e., native, non-transgenic). Back-crossing to a parental plant and out-crossing with a non-transgenic plant are also contemplated.

Modulating RecA Content and/or Composition

The present invention further provides a method for modulating (i.e., increasing or decreasing) RecA content or composition in a plant or part thereof. Modulation can be effected by increasing or decreasing the RecA content (i.e., the total amount of RecA) and/or the RecA composition (the ratio of various RecA monomers in the plant) in a plant. The method comprises transforming a plant cell with a recombinant expression cassette comprising a polynucleotide of the present invention as described above to obtain a transformed plant cell, growing the transformed plant cell under plant forming conditions, and inducing expression of a polynucleotide of the present invention in the plant for a time sufficient to modulate RecA content and/or composition in the plant or plant part.

In some embodiments, a recombinase in a plant may be modulated by altering, in vivo or in vitro, the promoter of a non-isolated RecA gene to up- or down-regulate gene expression. In some embodiments, the coding regions of native RecA genes can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate RecA content and/or composition in the plant. Plant forming conditions are well known in the art and discussed briefly, supra.

In general, content or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, lignification is modulated in monocots, particularly maize.

Molecular Markers

The present invention provides a method of genotyping a plant comprising a polynucleotide of the present invention. Preferably, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual,* Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R.G. Landis Company, Austin, Tex., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a RecA gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a RecA gene.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTR's and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 5 <G> 7 methyl GppppG cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. 96/19256. See also, Zhang, J.-H., et al. *Proc. Natl. Acad. Sci. USA* 94:45044509 (1997) and Zhao, et al., *Nature Biotech* 16:258–261 (1998). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an increased $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or 150% of the wild-type value.

Detection of Nucleic Acids

The present invention further provides methods for detecting a polynucleotide of the present invention in a nucleic acid sample suspected of comprising a polynucleotide of the present invention, such as a plant cell lysate, particularly a lysate of corn. In some embodiments, a RecA polynucleotide or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-RecA genes that would yield a false positive result.

Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer et al., *Biotechniques* 4(3): 230–250 (1986); Haase et al., *Methods in Virology*, Vol. VII, pp. 189–226 (1984); Wilkinson, The theory and practice of in situ hybridization in: *In situ Hybridization*, D. G. Wilkinson, Ed., IRL Press, Oxford University Press, Oxford; and *Nucleic Acid Hybridization: A Practical Approach*, Hames, B. D. and Higgins, S. J., Eds., IRL Press (1987).

Nucleic Acid Labels and Detection Methods

The means by which nucleic acids of the present invention are labeled is not a critical aspect of the present invention and can be accomplished by any number of methods currently known or later developed. Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

Nucleic acids of the present invention can be labeled by any one of several methods typically used to detect the presence of hybridized nucleic acids. One common method of detection is the use of autoradiography using probes labeled with $^3$H, 125I, $^{35}$S, $^{14}$C, or $^{32}$P, or the like. The choice of radio-active isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation. Labeling the nucleic acids of the present invention is readily achieved such as by the use of labeled PCR primers.

In some embodiments, the label is simultaneously incorporated during the amplification step in the preparation of the nucleic acids. Thus, for example, polymerase chain reaction (PCR) with labeled primers or labeled nucleotides will provide a labeled amplification product. In another embodiment, transcription amplification using a labeled nucleotide (e.g., fluorescein-labeled UTP and/or CTP) incorporates a label into the transcribed nucleic acids.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, (Renz. M., and Kurz, K., *A Colorimetric Method for DNA Hybridization, Nucl. Acids Res.* 12: 3435–3444 (1984)) and synthetic oligonucleotides have been coupled directly with alkaline phosphatase (Jablonski, E., et al., *Preparation of Oligodeoxynucleotide-Alkaline Phosphatase Conjugates and Their Use as Hybridization Probes, Nuc. Acids. Res.* 14: 6115–6128 (1986); and Li P., et al., *Enzyme-linked Synthetic Oligonucleotide probes: Non-Radioactive Detection of Enterotoxigenic Escherichia Coli in Faeca Specimens, Nucl. Acids Res.* 15: 5275–5287 (1987)).

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Antibodies to Proteins

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

A number of immunogens are used to produce antibodies specifically reactive with a protein of the present invention. An isolated recombinant, synthetic, or native RecA protein of 5 amino acids in length or greater and selected from a protein encoded by a polynucleotide of the present invention, such as exemplary sequences of SEQ ID NOS: 2, 4, 6, and 8 are the preferred immunogens (antigen) for the production of monoclonal or polyclonal antibodies. Those of skill will readily understand that the proteins of the present invention are typically denatured, and optionally reduced, prior to formation of antibodies for screening expression libraries or other assays in which a putative protein of the present invention is expressed or denatured in a non-native secondary, tertiary, or quarternary structure. Naturally occurring RecA polypeptides can be used either in pure or impure form.

The protein of the present invention is then injected into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an immunogen (antigen), preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, *Current Protocols in Immunology,* Wiley/Greene, NY (1991); and Harlow and Lane, *Antibodies: A Laboratory Manual,* Cold Spring Harbor Press, NY (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, preferably, 15 amino acids in length and more preferably the protein is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonals antibodies are screened for binding to a protein from which the immunogen was derived. Specific monoclonal and polyclonal antibodies will usually have an antibody binding site with an affinity constant for its cognate monovalent antigen at least between $10^6$–$10^7$, usually at least $10^8$, preferably at least $10^9$, more preferably at least $10^{10}$, and most preferably at least $10^{11}$ liters/mole.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology,* 4th ed., Stites et al, Eds., Lange Medical Publications, Los Altos, Calif., and references cited therein; Harlow and Lane, Supra; Goding, *Monoclonal Antibodies: Principles and Practice,* 2nd ed., Academic Press, New York, N.Y. (1986); and Kohler and Milstein, *Nature* 256: 495–497 (1975). Summarized briefly, this method proceeds by injecting an animal with an immunogen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of recombinant antibodies in phage or similar vectors (see, e.g., Huse et al., *Science* 246: 1275–1281 (1989); and Ward, et al., *Nature* 341: 544–546 (1989); and Vaughan et al., *Nature Biotechnology,* 14: 309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.,* 14: 845–851 (1996). Also, recombinant immunoglobulins may be produced. See, Cabilly, U.S. Pat. No. 4,816,567; and Queen et al., *Proc. Nat'l Acad. Sci.* 86: 10029–10033 (1989).

The antibodies of this invention are also used for affinity chromatography in isolating proteins of the present invention. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified protein are released.

The antibodies can be used to screen expression libraries for particular expression products such as normal or abnormal protein. Usually the antibodies in such a procedure are labeled with a moiety allowing easy detection of presence of antigen by antibody binding. Antibodies raised against a protein of the present invention can also be used to raise anti-idiotypic antibodies. These are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Protein Immunoassays

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology,* Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay,* Maggio, Ed., CRC Press, Boca Raton, Florida (1980); Tijan, Practice and Theory of Enzyme Immunoassays, *Laboratory Techniques in Biochemistry and Molecular Biology,* Elsevier Science Publishers B.V., Amsterdam (1985); Harlow and Lane, supra; *Immunoassay: A Practical Guide,* Chan, Ed., Academic Press, Orlando, Fla. (1987); *Principles and Practice of Immunoassaysm,* Price and Newman Eds., Stockton Press, NY (1991); and *Non-isotopic Immunoassays,* Ngo, Ed., Plenum Press, NY (1988). Immunological binding assays (or immunoassays) typically utilize a "capture agent" to specifically bind to and often immobilize the analyte (in this case, a protein of the present invention). The capture agent is a moiety that specifically binds to the analyte. In a preferred embodiment, the capture agent is an antibody that specifically binds a protein(s) of the present invention. The antibody may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled protein of the present invention or a labeled antibody specifically reactive to a protein of the present invention. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (See, generally Kronval, et al., *J. Immunol.* 111: 1401–1406 (1973), and Akerstrom, et al., *J. Immunol.* 135: 2589–2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting a protein of the present invention in a biological sample generally comprises the steps of contacting the biological sample with an antibody which specifically reacts, under immunologically reactive conditions, to a protein of the present invention. The antibody is allowed to bind to the protein under immunologically reactive conditions, and the presence of the bound antibody is detected directly or indirectly.

A. Non-Competitive Assay Formats

Immunoassays for detecting proteins of the present invention include competitive and noncompetitive formats. Noncompetitive immunoassays are assays in which the amount of captured analyte (i.e., a protein of the present invention) is directly measured. In one preferred "sandwich" assay, for example, the capture agent (e.g., an antibody specifically reactive, under immunoreactive conditions, to a protein of the present invention) can be bound directly to a solid substrate where they are immobilized. These immobilized antibodies then capture the protein present in the test sample. The protein thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

B. Competitive Assay Formats

In competitive assays, the amount of analyte present in the sample is measured indirectly by measuring the amount of an added (exogenous) analyte (e.g., a protein of the present invention) displaced (or competed away) from a capture agent (e.g., an antibody specifically reactive, under immunoreactive conditions, to the protein) by the analyte present in the sample. In one competitive assay, a known amount of analyte is added to the sample and the sample is then contacted with a capture agent that specifically binds a protein of the present invention. The amount of protein bound to the capture agent is inversely proportional to the concentration of analyte present in the sample.

In a particularly preferred embodiment, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein.

A hapten inhibition assay is another preferred competitive assay. In this assay a known analyte, (such as a protein of the present invention) is immobilized on a solid substrate. A known amount of antibody specifically reactive, under immunoreactive conditions, to the protein is added to the sample, and the sample is then contacted with the immobilized protein. In this case, the amount of antibody bound to the immobilized protein is inversely proportional to the amount of protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

C. Generation of Pooled Antisera for use in Immunoassays

A protein that specifically binds to or that is specifically immunoreactive with an antibody generated against a defined immunogen, such as an immunogen consisting of the amino acid sequence of SEQ ID NOS: 2, 4, 6, and 8 is determined in an immunoassay. The immunoassay uses a polyclonal antiserum which is raised to a polypeptide of the present invention (i.e., the immunogenic polypeptide). This antiserum is selected to have low crossreactivity against other proteins and any such crossreactivity is removed by immunoabsorbtion prior to use in the immunoassay (e.g., by immunosorbtion of the antisera with a protein of different substrate specificity (e.g., a different enzyme) and/or a protein with the same substrate specificity but of a different form).

In order to produce antisera for use in an immunoassay, a polypeptide (e.g., SEQ ID NOS: 2, 4, 6, and 8) is isolated as described herein. For example, recombinant protein can be produced in a mammalian or other eukaryotic cell line. An inbred strain of mice is immunized with the protein of using a standard adjuvant, such as Freund's adjuvant, and a standard mouse immunization protocol (see Harlow and Lane, supra). Alternatively, a synthetic polypeptide derived from the sequences disclosed herein and conjugated to a carrier protein is used as an immunogen. Polyclonal sera are collected and titered against the immunogenic polypeptide in an immunoassay, for example, a solid phase immunoassay with the immunogen immobilized on a solid support. Polyclonal antisera with a titer of $10^4$ or greater are selected and tested for their cross reactivity against polypeptides of different forms or substrate specificity, using a competitive binding immunoassay such as the one described in Harlow and Lane, supra, at pages 570–573. Preferably, two or more distinct forms of polypeptides are used in this determination. These distinct types of polypeptides are used as competitors to identify antibodies which are specifically bound by the polypeptide being assayed for. The competitive polypeptides can be produced as recombinant proteins and isolated using standard molecular biology and protein chemistry techniques as described herein.

Immunoassays in the competitive binding format are used for crossreactivity determinations. For example, the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent crossreactivity for the above proteins is calculated, using standard calculations. Those antisera with less than 10% crossreactivity with a distinct form of a polypeptide are selected and pooled. The cross-reacting antibodies are then removed from the pooled antisera by immunoabsorbtion with a distinct form of a polypeptide.

The immunoabsorbed and pooled antisera are then used in a competitive binding immunoassay as described herein to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

D. Other Assay Formats

In a particularly preferred embodiment, Western blot (immunoblot) analysis is used to detect and quantify the presence of protein of the present invention in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a protein of the present invention. The antibodies specifically bind to the protein on the solid support. These antibodies may be directly labeled or alternatively may be subsequently detected using labeled antibodies (e.g., labeled sheep anti-mouse antibodies) that specifically bind to the antibodies.

E. Quantification of Proteins

The proteins of the present invention may be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

F. Reduction of Non-Specific Binding

One of skill will appreciate that it is often desirable to reduce non-specific binding in immunoassays and during analyte purification. Where the assay involves an antigen, antibody, or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used.

G. Immunoassay Labels

The labeling agent can be, e.g., a monoclonal antibody, a polyclonal antibody, a binding protein or complex, or a polymer such as an affinity matrix, carbohydrate or lipid. Detectable labels suitable for use in the present invention include any composition detectable by spectroscopic, radioisotopic, photochemical, biochemical, immunochemical, electrical, optical or chemical means. Detection may proceed by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes, radiolabels, enzymes, and colorimetric labels or colored glass or plastic beads, as discussed for nucleic acid labels, supra.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length RecA polypeptide (e.g., enzyme). Generally, the polypeptide will be present in a range sufficient to determine the effect of the compound, typically about 1 nM to 10 $\mu$M. Likewise, the compound will be present in a concentration of from about 1 nM to 10 $\mu$M. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics is well known in the art. See, e.g., Segel, *Biochemical Calculations*, $2^{nd}$ ed., John Wiley and Sons, New York (1976).

Although the present invention has been described in some detail by way of illustration and example for purposes of clarity of understanding, it will be obvious that certain changes and modifications may be practiced within the scope of the appended claims.

EXAMPLE 1

This example describes the construction cDNA libraries.
Total RNA Isolation

Total RNA was isolated from corn tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem.* 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.
Poly(A)+ RNA Isolation The selection of poly(A)+ RNA from total RNA was performed using PolyATtract system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.
cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2

This example describes cDNA sequencing and library subtraction.
Sequencing Template Preparation Individual colonies were picked and DNA was prepared either by PCR with M13 forward primers and M13 reverse primers, or by plasmid isolation. All the cDNA clones were sequenced using M13 reverse primers.
Q-bot Subtraction Procedure cDNA libraries subjected to the subtraction procedure were plated out on 22×22 $cm^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 $cm^2$ nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., in Molecular Cloning: A laboratory Manual, $2^{nd}$ Edition). The following probes were used in colony hybridization:
1. First strand cDNA from the same tissue as the library was made from to remove the most redundant clones.
2. 48–192 most redundant cDNA clones from the same library based on previous sequencing data.
3. 192 most redundant cDNA clones in the entire corn sequence database.
4. A Sal-A20 oligo nucleotide: TCG ACC CAC GCG TCC GAA AAA MA AAA AAA AAA AAA, listed in SEQ ID NO. 9, removes clones containing a poly A tail but no cDNA.

5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3
Identification and Sequencing of Maize RecA cDNAs

Four bacterial RecA homologues, designated Rec1ma, Rec2ma, Rec3ma and Rec4ma (SEQ ID NOS: 1, 3, 5, and 7 or Tables 1, 2, 3, and 4), were identified from the maize genomics database described above, based on their sequence homology to known bacterial RecA genes. The "P-loop" or ATP/GTP binding sequence (underlined) and the RecA signature sequence (italics and underlined) are conserved in all RecA sequences known thus far are identified. The signature sequence is a 27 nucleotide or 9 amino acid sequence found in all RecA molecules sequenced thus far. The signature sequence is as follows: A-L-[KR]-[IF]-[FY]-[STA]-[STAD]-[LIVM]-R (SEQ ID NO: 10). Residues A, L, and R appear to be invariable The residues in the brackets are interchangeable (for example: K or R; F or Y). See also Smith, et al., *Bio Essays* 10:12–16 (1.989); Miller, et al., *Annu Rev Microbiol* 44:365–394 (1990); and Lloyd, et al., *J Mol Evol* 37:399–407 (1993). These identified sequences are used as probes for cloning full length cDNA and genomic clones.

EXAMPLE 4
Mapping of the Maize RecA Clones

Probe fragments are generated that are identical to the original maize RecA genes. In order to make these probe fragments, sequence-specific hybridization, oligonucleotide primers specific to unique portions of the RecA genes are synthesized and used in conjunction with an M13 universal sequencing primer to PCR amplify probe fragments from the RecA gene sequence. These fragments, which extend from just downstream of the translation stop codon to the end of the poly(A) tail of the cDNA sequences, are used as probes against two maize populations and map positions are determined.

Southern hybridizations is carried out using two different maize populations generated as part of a breeding program. Population 1 (MARSA—Marker Assisted Recombination Selection population), an F4, is generated from crosses of the lines R03×N46, and will include 200 individuals as part of the mapping family. Population 2 (ALEB9), an F2, is generated from crosses of the lines R67×P38 and contains 240 individuals. DNA is isolated from each individual by a CTAB extraction method (Saghai-Maroof et al., *Proc. Nat'l Acad. Sci. (U.S.A.)*, 81:8014–8018 (1994)) and then digested individually with restriction enzymes BamHI, HindIII, EcoRI and EcoRV. Digests are separated on agarose gels and transferred to membranes (Southern, *J. Molec. Biol.*, 98:503–517 (1975)) prior to hybridization (Helentjaris et al., *Plant Mol. Biol.*, 5:109–118 (1985)) with an array of probes to establish the basic RFLP map. Population 1 membranes are hybridized using 179 RFLP probes, while population 2 membranes are hybridized using 115 RFLP probes. After hybridization the membranes are exposed to x-ray film for an appropriate length of time to be visually scored. All data is entered into an electronic database and map positions of the RFLP probes (Evola et al., *Theor. Appl. Genet.*, 71:765–771(1986)) are determined using MAPMAKER (Lincoln et al, in *Constructing Genetic Linkage Maps with MAPMARKER/EXP Version 3.0: A Tutorial and Reference Manual*, Whitehead Institute for Biomedical Research, Cambridge, Mass. (1993)) and a map is constructed for each population.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

TABLE 1

Nucleotide Sequence of Zea mays RecA-like gene - 1(Rec1ma)

```
  1 TCAAGGCATTTGGGCATCTCACACTTCTTCGCCTTCCTTTAATGGATGACTTATCTGCTT   60
                                                  MetThrTyrLeuLeu

61 GAAATATTATTATACCTTTTGAATTTTGACGCATTACGATGTTGCTTTGGTTTGTCACTA  120
    GluIleLeuLeuTyrLeuLeuAsnPheAspAlaLeuArgCysCysPheGlyLeuSerLeu

121 AGAGATATTTATTCACAATTTCATCTGCAGCAAAAAGTTCTTGATGCCGCTATGAATGAC  180
    ArgAspIleTyrSerGlnPheHisLeuGlnGlnLysValLeuAspAlaAlaMetAsnAsp

181 ATAAACAACTCTTTTGGAAAAGGAAGTGTTACAAGATTAGGCAGTGCTGGTGGTGCTTTT  240
    IleAsnAsnSerPheGlyLysGlySerValThrArgLeuGlySerAlaGlyGlyAlaPhe

241 GTGGAGACATTCCCAAGTGGTTGTCTAACACTAGATTTTGCTCTGGGTGGCGGTCTTCCA  300
    ValGluThrPheProSerGlyCysLeuThrLeuAspPheAlaLeuGlyGlyGlyLeuPro

301 AAAGGAAGAGTAGTGGAGGTATATGGTCCAGAAAGCAGTGGAAAGACTACCCTAGCTTTG  360
    LysGlyArgValValGluValTyrGlyProGluSerSerGlyLysThrThrLeuAlaLeu

361 CATGCAATTGCTGAAATACAGAAGCTTGGAGGAAATGCCATGCTTGTCGATGCAGAGCAT  420
    HisAlaIleAlaGluIleGlnLysLeuGlyGlyAsnAlaMetLeuValAspAlaGluHis
```

TABLE 1-continued

Nucleotide Sequence of Zea mays RecA-like gene - 1(Rec1ma)

```
 421 GCTTTTGATCCAGCTTATTCAAAAGCTCTTGGGGTAGATATTGAAAATCTGATTGTCTGC
     AlaPheAspProAlaTyrSerLysAlaLeuGlyValAspIleGluAsnLeuIleValCys

481 CAGCCTGACAACGGAGAGATGGCACTAGAAATTGCGGACCGTATGTGCAGATCTGGAGCA
     GlnProAspAsnGlyGluMetAlaLeuGluIleAlaAspArgMetCysArgSerGlyAla

541 ATAGATCTTATCTGTATTGATTCGGTGTCAGCGCTCACCCCACGTGCAGAAATTGAAGGT
     IleAspLeuIleCysIleAspSerValSerAlaLeuThrProArgAlaGluIleGluGly

601 GAGATAGGAATGCAGCAGATGGGTCTACAAGCTCGTCTGATGAGTCAAGCATTGAGAAAA
     GluIleGlyMetGlnGlnMetGlyLeuGlnAlaArgLeuMetSerGlnAlaLeuArgLys

661 ATGTCAGGCAATGCCTCAAAGGCTGGCTGTACTCTTATGTTCTTGAATCAAATAAGATAC
     MetSerGlyAsnAlaSerLysAlaGlyCysThrLeuMetPheLeuAsnGlnIleArgTyr

721 AAGATTGGAGTGTTCTATGGGAATCCTGAAGTCACTAGTGGAGGGATAGCCTTGAAATTC
     LysIleGlyValPheTyrGlyAsnProGluValThrSerGlyGlyIleAlaLeuLysPhe

781 TTTGCATCTGTCCGTCTTGAGATACGGCTCATTGGGAAGATAAAATCTGCCAAGGGAGAT
     PheAlaSerValArgLeuGluIleArgLeuIleGlyLysIleLysSerAlaLysGlyAsp

841 GAAGATGTTGGTGTGAAGGTTCGTGTCAGAGTGCAGAAGAGTAAAGTATCTAGGCCCTAC
     GluAspValGlyValLysValArgValArgValGlnLysSerLysValSerArgProTyr

901 AAGCAAGCTGAATTTGAAATCATTTTTGGGGAGGGTGTTAGTAAATTGGGGTGCGTTCTT
     LysGlnAlaGluPheGluIleIlePheGlyGluGlyValSerLysLeuGlyCysValLeu

961 GATTGTGCTGAGCTGATGGATGTAGTTGCAAAGAAGGGTTCGTGGTACAGCTACAAAGAT
     AspCysAlaGluLeuMetAspValValAlaLysLysGlySerTrpTyrSerTyrLysAsp

1021 ATAAGATTGGGCCAAGGCAGAGAGAAGGCACTGCAGTATCTCCGAGAGAGCCCAACCACC
     IleArgLeuGlyGlnGlyArgGluLysAlaLeuGlnTyrLeuArgGluSerProThrThr

1081 TGCGATGAGATAGAAAAGGTGGTTCGAGCTATGATTCCAGAAGGATCCAGACATATGAGC
     CysAspGluIleGluLysValValArgAlaMetIleProGluGlySerArgHisMetSer

1141 CTACTAGCTTTCGGGCAGTCATCATCAACTGAAGATGAACAGGCGTATGATGAACAATAA
     LeuLeuAlaPheGlyGlnSerSerSerThrGluAspGluGlnAlaTyrAspGluGlnEnd

1201 TGGTACATGAGGTTCCGAAGATGGAACACTTGTGAAACCGTCAAGCTCTGGCTTGTGTCC

1261 CTTGCGGATAACAGAAAAGATCAGAGGTAACCAATCAATATGGCAGTTGTGTGAGCGCTG

1321 GAGTGGAGTTGACTAAGACCTTGTTCGTTTCTGGTGGATTGGTGGGTCCTAACGATTCCT

1381 GACCGGATTGTTTCTCTAATTTATATAAACTTTGATTAGCTGGAACGATTCCGGGTGCAA

1441 TCCGACGGAAATGAACAAGGCCTAATGTTGTATGTGTACTGTGGCATGGCAGAACCGTCC

1501 GGTTTAACCCAAAA           1514
```

TABLE 2

Nucleotide sequence of Zea mays RecA-like gene - 2 (Rec2ma)

```
  1 AATTCGGCACGAGAGACAACACTCGCGCTTCATGTTATTAAGGAAGCTCAAAAGAATGGA   60
    AsnSerAlaArgGluThrThrLeuAlaLeuHisValIleLysGluAlaGlnLysAsnGly

61 GGTTATTGTGCTTATATTGATGCAGAAAATGCCTTCAACCCTTCATTTGCTGAATCTATT  120
    GlyTyrCysAlaTyrIleAspAlaGluAsnAlaPheAsnProSerPheAlaGluSerIle

121 GGCGTAGACAGTGAAAGGCTCTTGATAGCCCAACCTGATTCTGCTGAAAATTCTCTAAGC  180
    GlyValAspSerGluArgLeuLeuIleAlaGlnProAspSerAlaGluAsnSerLeuSer

181 ATTGTAAACACTCTTGTTGGTGGTTCTGTTGCTGTTGTTGTTGTGGACAGTGTGGCAGCA  240
    IleValAsnThrLeuValGlyGlySerValAlaValValValValAspSerValAlaAla

241 CTTATTCCCAAATGTGAAATTGAAGGTGAAATATACACAAATTGTGGAGACATCCAATCC  300
    LeuIleProLysCysGluIleGluGlyGluIleTyrThrAsnCysGlyAspIleGlnSer

301 CATTTGATGACTCGGGCCCTTAGAAAAATTCAGTACACTTTATGTCGATCTGAAACACTT  360
    HisLeuMetThrArgAlaLeuArgLysIleGlnTyrThrLeuCysArgSerGluThrLeu

361 ATTATTTTTGTGAATCAGGTTAGAACAAAGCGGACATCAAGTAATCCTGGGATCTACAAG  420
    IleIlePheValAsnGlnValArgThrLysArgThrSerSerAsnProGlyIleTyrLys

421 GAGGTGCCTTGCGGTGGTAATGCACTAGGATTCTATGCTGCAGTCAGAATGAGGACTTCA  480
    GluValProCysGlyGlyAsnAlaLeuGlyPheTyrAlaAlaValArgMetArgThrSer

481 AGGAGAGAACTGCGCTATAGTGAAGATGAGGCTACCGGCGTAGGTATATCAGTGCAGATC  540
    ArgArgGluLeuArgTyrSerGluAspGluAlaThrGlyValGlyIleSerValGlnIle

541 ATCAAGAACAAATTGGCTCCAGCGAACCTGAAGAAGGAAGCCGGCATCGACATCACATTC  600
    IleLysAsnLysLeuAlaProAlaAsnLeuLysLysGluAlaGlyIleAspIleThrPhe

601 GGTAAGGGGATCTGCCACGAGTCGGAGATCCTGGAGACGGCTTCCTCCGTCGGAGTGATC  660
    GlyLysGlyIleCysHisGluSerGluIleLeuGluThrAlaSerSerValGlyValIle

661 CTGAAAGACGGGTGTGGGTATTGGATCAACAACGAGTTCCTGGCAGGCAAGGTGGAAGCG  720
    LeuLysAspGlyCysGlyTyrTrpIleAsnAsnGluPheLeuAlaGlyLysValGluAla

721 GAGAAGTTCCTGCGTGAAAACGCTGCAGTGGCAGATGAGATCTGCAATACCGTGAGGAAC  780
    GluLysPheLeuArgGluAsnAlaAlaValAlaAspGluIleCysAsnThrValArgAsn

781 GAGTTCTTGCAAAGGTGA                                            798
    GluPheLeuGlnArgEnd
```

TABLE 3

Nucleotide Sequence of Zea mays RecA-like gene - 3 (Rec3ma)

```
  1 GAATTCCCGGGTCGACCCACGCGTCCGAAACCCCTAAACCCTAGCTCCCCACCCCCAGCC   60

61 TCCCCGCGGCTTCCAGCGATTGGAGGCGAAGCAGCCGCCATGGCGATCCTCCTTAGGCGC  120
                                    MetAlaIleLeuLeuArgArg

121 GCGTCGCTGCGGCGCGTCATCGCCTTCGCCGCCGCCTCCTCCTCCTCCTCTTCTTTGCAC  180
    AlaSerLeuArgArgValIleAlaPheAlaAlaAlaSerSerSerSerSerSerLeuHis

181 TCTGAGATTTATAAGCAAGGGGTTTGTGGATCCATGTTTCATTGCCGAGAGTTCGCATCA  240
    SerGluIleTyrLysGlnGlyValCysGlySerMetPheHisCysArgGluPheAlaSer
```

TABLE 3-continued

Nucleotide Sequence of Zea mays RecA-like gene - 3 (Rec3ma)

```
 241 AAAGCCAAAAAAAAGAAGTCAAGTGGAACAGACTCCGATGAGGAGTATGTCAAAGAAA  300
     LysAlaLysLysLysLysSerSerGlyThrAspSerAspGluGluSerMetSerLysLys

301 GACTTGGCTTTACACCAGGCTATCGATCAAATAACGTCTGCATTTGGGAAGGGGCAATA  360
     AspLeuAlaLeuHisGlnAlaIleAspGlnIleThrSerAlaPheGlyLysGlyAlaIle

361 ATGTGGCTTGGGCGTTCGCAAGGCCTTAGAGATGTACCTGTTGTGTCTACTGGGTCTTTC  420
     MetTrpLeuGlyArgSerGlnGlyLeuArgAspValProValValSerThrGlySerPhe

421 GCTTTGGATATGGCTCTAGGAACTGGTGGTCTTCCAAAGGGGCGTGTCATAGAGGTCTAT  480
     AlaLeuAspMetAlaLeuGlyThrGlyGlyLeuProLysGlyArgValIleGluValTyr

481 GGTCCAGAGGCTTCAGGCAAGACAACACTTGCTCTACATGTCATTGCAGAAGCACAAAAG  540
     GlyProGluAlaSerGlyLysThrThrLeuAlaLeuHisValIleAlaGluAlaGlnLys

541 AATGGGGGTTACTGTGCCTTTGTAGATGCAGAACACGCTTTGGATCCAGCTCTTGCAGAG  600
     AsnGlyGlyTyrCysAlaPheValAspAlaGluHisAlaLeuAspProAlaLeuAlaGlu

601 TCAATTGGTGTTGACACTAACAATTTGCTCGTCTCTCAGCCAGACTGCGCTGAGCAAGCA  660
     SerIleGlyValAspThrAsnAsnLeuLeuValSerGlnProAspCysAlaGluGlnAla

661 CTCAGTCTTGTGGACACACTGATTCGAAGTGGATCTGTTGATGTTGTTGTAGTAGACAGT  720
     LeuSerLeuValAspThrLeuIleArgSerGlySerValAspValValValValAspSer

721 GTAGCTGCGCTTGTTCCAAAGACTGAGCTTGATGGTGAGATGGGTGATGCACATGTTGCT  780
     ValAlaAlaLeuValProLysThrGluLeuAspGlyGluMetGlyAspAlaHisValAla

781 CTTCAGGCTAGGTTGATGAGCCAAGCTCTTCGCAAGCTTAGCCACTCACTTTCACTTTCG  840
     LeuGlnAlaArgLeuMetSerGlnAlaLeuArgLysLeuSerHisSerLeuSerLeuSer

841 CAGACAGTTTTGTTATTTATTAATCAGATCAGGGCCAAGGTAGCCACATTTGGATTTGGA  900
     GlnThrValLeuLeuPheIleAsnGlnIleArgAlaLysValAlaThrPheGlyPheGly

901 GGACCAACTGAGGTCACTTCTGGTGGTAACGCCTTGAAGTTTTATGCTTCTGTTCGCTTG  960
     GlyProThrGluValThrSerGlyGlyAsnAlaLeuLysPheTyrAlaSerValArgLeu

961 AACATCAGGCGTATTGGTTTTTTAAAGGAAGGTGAAGAGACAATAGGTAGTCAGGTTGCT 1020
     AsnIleArgArgIleGlyPheLeuLysGluGlyGluGluThrIleGlySerGlnValAla

1021 GTGAAGATTGTAAAAAATAAGCATGCCCCACCCTTCAAGACTGCACAGTTTGAGCTTGAA 1080
     ValLysIleValLysAsnLysHisAlaProProPheLysThrAlaGlnPheGluLeuGlu

1081 TTTGGAAAGGGGATATGCCGCAGTTCTGAGCTTTTTGAACTTGGGTTGAAGCACAAGCTT 1140
     PheGlyLysGlyIleCysArgSerSerGluLeuPheGluLeuGlyLeuLysHisLysLeu

1141 ATCCAAAAGACTGGCGGTGCATATTATAGATTCAATGATATGAGTTTCAAAGGTAAAAAT 1200
     IleGlnLysThrGlyGlyAlaTyrTyrArgPheAsnAspMetSerPheLysGlyLysAsn

1201 AACCTTAAATCTTACCTTACTGAAAACAAGAGTGTTGCAAATGATCTGGAGACGAAACTA 1260
     AsnLeuLysSerTyrLeuThrGluAsnLysSerValAlaAsnAspLeuGluThrLysLeu

1261 AGGAGATTGATGGGAACCGAAGCACCTAAAGAGCAGGAGGCAGAAGACGTTCGCCGAGT 1320
     ArgArgLeuMetGlyThrGluAlaProLysGluGlnGluAlaGluAspSerSerProSer

1321 GATTTGCCTGAAGAGGTTGTCACACCTGAAGCATCCTCAGAAGAGGATATGGGAGTCGTA 1380
     AspLeuProGluGluValValThrProGluAlaSerSerGluGluAspMetGlyValVal
```

TABLE 3-continued

Nucleotide Sequence of Zea mays RecA-like gene - 3 (Rec3ma)

```
1381 ATCGAGGCTTGACCAGTGATCTGACGTGCTGGCAAGCGAGACCAGAATTTCTGGAGCTGT 1440
     IleGluAlaEnd

1441 TCCTGTAAAACAATATTTTGGGTCCTGAAGTCACCACCGCTTGGATCGACATGACCCTGC 1500

1501 GGTGTTCTGGTGATTCCATTGTAACAGACTTCAGCCCTTACCGTGCTTTTACAGTAGTGT 1560

1561 AGCATGAAGAGAATTGGCATTGTGTGAAATCATGCTGATAGCTGAGAGGTGGAAGTTGAA 1620

1621 GGCGGTAAGGTTGTGGTCTCTGGCTATCTGAACTCTAGTGTAGTATATAGTGTAGGCGAC 1680

1681 GGTAAAATGTAGTGGCGTGGTCGTGTATACATGATGCTCACATTTTGAGCTCCTGGTTTC 1740

1741 ACGTCGAAGCCAATTTCAAAAGCATTCTTTATTGAGCGCAGCTAGAATTACATCGAAAAA 1800

1801 AAAAAAAAAAAAAAAAAAAAAAAAAAAA                                 1828
```

TABLE 4

Nucleotide sequence of Zea mays RecA-like gene 4 (Rec4ma)

```
1    AATTCGGCACGAGAAAACCCCTAAACCCTAGCCCCTCACCTCTCGCCTCCGCCCTCATCC  60

61   GCGCGACTTGCAGCGGTTGGAGGCGAAGCCGGCTCCATGACGACCCTCCTCAGGCGCGCG  120
                                       MetThrThrLeuLeuArgArgAla

121  TCGCTGCGGCGCGTCATTGCCGCCGCCGCCGCCTCTTCTTTTCACCCTGAGAGCTATAAG  180
     SerLeuArgArgValIleAlaAlaAlaAlaAlaSerSerPheHisProGluSerTyrLys

181  CAAGGGATCTGTGGCTCCACATTTCATTGCCGAGAGTTCGCATCAAAAGCAAAAAAGAAG  240
     GlnGlyIleCysGlySerThrPheHisCysArgGluPheAlaSerLysAlaLysLysLys

241  TCAAGTGGAACAGACTCTGGGGAGGAGAACATGTCAAAGAAAGACTTGGCTTTACACCAG  300
     SerSerGlyThrAspSerGlyGluGluAsnMetSerLysLysAspLeuAlaLeuHisGln

301  GCTATTGATCAGATAACGTCTGCATTTGGGAAGGGGCAATAATGTGGCTTGGGCGTTCA   360
     AlaIleAspGlnIleThrSerAlaPheGlyLysGlyAlaIleMetTrpLeuGlyArgSer

361  CAAGGCCATAGAGATGTACCAGTCGTGTCTACTGGGTCTTTGGATTTGGATATGGCTCTA  420
     GlnGlyHisArgAspValProValValSerThrGlySerLeuAspLeuAspMetAlaLeu

421  GGAACTGGTGGTCTTCCAAAGGGGCGTGTTGTAGAGGTATATGGTCCAGAGGCATCAGGC  480
     GlyThrGlyGlyLeuProLysGlyArgValValGluValTyrGlyProGluAlaSerGly

481  AAGACAACGCTTGCTCTACATGTCATTGCAGAAGCACAAAAGAATGGAGGTTACTGTGCC  540
     LysThrThrLeuAlaLeuHisValIleAlaGluAlaGlnLysAsnGlyGlyTyrCysAla

541  TTTGTACATGCAGAGCACGCTTTGGATCCAGCTCTCGCCGAGTCAATTGGTGTTGACACT  600
     PheValAspAlaGluHisAlaLeuAspProAlaLeuAlaGluSerIleGlyValAspThr

601  AACAATTTACTCCTTTCTCAGCCCGATTGTGCTGAGCAGGCACTCAGTCTTGTGGACACA  660
     AsnAsnLeuLeuLeuSerGlnProAspCysAlaGluGlnAlaLeuSerLeuValAspThr

661  CTGATTCGAAGTGGATCTGTTGATGTTGTTGTAGTAGACAGTGTTGCTGCGCTTGTTCCA  720
     LeuIleArgSerGlySerValAspValValValValAspSerValAlaAlaLeuValPro
```

TABLE 4-continued

Nucleotide sequence of Zea mays RecA-like gene 4 (Rec4ma)

```
 721 AAGACTGAGCTTGATGGTGAGATGGGTGATGCACATGTTGCTCTTCAGGCTAGGTTGATG   780
     LysThrGluLeuAspGlyGluMetGlyAspAlaHisValAlaLeuGlnAlaArgLeuMet

781 AGTCAAGCCCTTCGCAAGCTTAGCCACTCCCTTTCACTTTCGCAAACAATTTTGTTATTT   840
     SerGlnAlaLeuArgLysLeuSerHisSerLeuSerLeuSerGlnThrIleLeuLeuPhe

841 ATTAATCAGATCAGGGCCAAGGTAGCCACATTTGGATTTGGAGGACCAACTGAGGTTACT   900
     IleAsnGlnIleArgAlaLysValAlaThrPheGlyPheGlyGlyProThrGluValThr

901 TCTGGTGGCAACGCCTTGAAGTTTTATGCGTCTGTTCGCTTGAACATCAGGCGTATTGGT   960
     SerGlyGlyAsnAlaLeuLysPheTyrAlaSerValArgLeuAsnIleArgArgIleGly

961 TTGGTAAAGAAAGGCGAAGAGACAATAGGTAGTCACATTGCTGTGAAGATTGTAAAAAAC  1020
     LeuValLysLysGlyGluGluThrIleGlySerGlnIleAlaValLysIleValLysAsn

1021 AAGCATCCCCCACCCTTCAAGACTGCACAGTTTGAGCTTGAATTTGGAAAGGGGATATGC  1080
     LysHisAlaProProPheLysThrAlaGlnPheGluLeuGluPheGlyLysGlyIleCys

1081 CGCAGTTCTGAGCTTTTTGAACTTGGATTGAAGCATAAGCTTATCCGAAAGAGTGGTGGT  1140
     ArgSerSerGluLeuPheGluLeuGlyLeuLysHisLysLeuIleArgLysSerGlyGly

1141 TCATATTATAGTTTCAATGGTAAGGCTTTCAATGGTAAAAGTAACCTTAAATCTTACCTT  1200
     SerTyrTyrSerPheAsnGlyLysAlaPheAsnGlyLysSerAsnLeuLysSerTyrLeu

1201 ACTGAAAACAAGAGCGTTGCAAATGATCTGGAGATGGAACTAAAGAGATTGATGGGAACT  1260
     ThrGluAsnLysSerValAlaAsnAspLeuGluMetGlyLeuLysArgLeuMetGlyThr

1261 GATGCGTCTAAAGAGCAGGAGGCAGGAGACAGTTCGCAGAGTGATTTGCCTGAAGAGAGT  1320
     AspAlaSerLysGluGlnGluAlaGlyAspSerSerGlnSerAspLeuProGluGluSer

1321 GTCACACCTGAAGCATCGTCAGAAGAGGATCTGGGAGCCATAATTGAAGGTTAGCCAGTG  1380
     ValThrProGluAlaSerSerGluGluAspLeuGlyAlaIleIleGluGlyEnd

1381 ATCTGATGTGCTGGCAAGTGGGAACAGAATTTCTGGACTCTGGAGCAGTTGTTCCTGTAA  1440

1441 AACAATATCTTGGGTCCTGAAGTCACCACCGTTTGGATCGACATGCCCTGTGGTGTTCTG  1500

1501 GTGATCTCATCGTAGCAGACTTCAGTCTTTACTGTGCTTATACAGTAGTGCAGCAGGAAG  1560

1561 AGAATTCACATTGTGTGAAATCATGGTGATAGCTGAGAGGTGGAAGTTGAAGTAAGCCGG  1620

1621 GAAGGGTGAGGTATTGTGGTCCGTGCCATTTAAACTTCAGTAACCAAACGTCGTGTATAT  1680

1681 ATCATGTGCACATTTTAAAACGGGCATTCTTTATTGACTGCTGCTTAGATTTACATTCA   1740

1741 GCTCCCTCCACTTCCAAAAAAAAAAAAAAAAA                              1773
```

What is claimed is:

1. An isolated nucleic acid encoding a polypeptide with RecA activity comprising a member selected from the group consisting of:
   a) a first polynucleotide having at least 80% sequence identity to a second polynucleotide encoding a polypeptide selected from the group consisting of SEQ ID NOS: 2, 4, 6, 8, wherein the percent sequence identity is determined by the GAP algorithm under default parameters over the entire coding region of the second polynucleotide; and
   b) a polynucleotide which is fully complementary to said first polynucleotide of (a).

2. The isolated nucleic acid of claim 1, wherein said member has a sequence selected from the group consisting of SEQ ID NOS: 1, 3, 5, and 7.

3. A recombinant expression cassette, comprising the isolated nucleic acid of claim 1 operably linked to a promoter.

4. A recombinant expression cassette comprising a nucleic acid sequence selected from the group consisting of SEQ ID NO:1, 3, 5, and 7, wherein said nucleic acid sequence is operably linked in antisense orientation to a promoter.

5. A host cell transformed with the isolated nucleic acid of claim 1.

6. The host cell of claim 5, wherein said host cell is a sorghum (*Sorghum bicolor*), maize (*Zea mays*), rice (*Oryza sativa*), or wheat (*Triticum aestivum*) cell.

7. The isolated nucleic acid of claim 1, wherein said member is DNA.

8. An isolated nucleic acid comprising a polynucleotide of at least 50 nucleotides in length which selectively hybridizes under stringent conditions and a wash of 0.1×SSC, 0.1% SDS at 65° C. to a nucleic acid selected from the group consisting of SEQ ID NOS: 1, 3, 5, and 7 or a nucleic acid fully complementary thereof.

9. The isolated nucleic acid of claim 8 operably linked to a promoter.

10. An isolated nucleic acid comprising a polynucleotide encoding a polypeptide with RecA activity, said polynucleotide having at least 80% sequence identity to a polynucleotide selected from the group consisting of SEQ ID NOS, 1, 3, 5, and 7 or a nucleic acid fully complementary thereof, wherein the percent sequence identity is determined by the GAP algorithm under default parameters over the entire coding region.

11. A transgenic plant comprising a recombinant expression cassette comprising a plant promoter operably linked to an isolated nucleic acid of claim 1.

12. The transgenic plant of claim 11, wherein said plant is *Zea mays*.

13. A transgenic seed from the transgenic plant of claim 11.

14. The transgenic seed of claim 13, wherein the plant is *Zea mays*.

15. A method of modulating RecA in a plant, comprising:
   (a) transforming a plant cell with a recombinant expression cassette comprising the isolated nucleic acid of claim 1 operably linked to a promoter, wherein the polynucleotide is in sense orientation;
   (b) growing the plant cell under plant growing conditions to produce a transformed plant; and
   (c) inducing expression of said polynucleotide for a time sufficient to modulate RecA in said transformed plant.

16. The method of claim 15, wherein the plant is maize.

17. The method of claim 15, wherein RecA is increased.

18. A transformed plant cell from the transformed plant produced by the method of claim 15.

19. A transgenic plant produced by the method of claim 15.

20. A transgenic seed produced by the plant of claim 19.

21. The plant of claim 19, wherein the plant is selected from the group consisting of: maize, soybean, sunflower, sorghum, canola, wheat, alfalfa, cotton, rice, barley, and millet.

* * * * *

UNITED STATES PATENT AND TRADEMARK OFFICE
CERTIFICATE OF CORRECTION

| | | |
|---|---|---|
| PATENT NO. | : 6,388,169 B1 | Page 1 of 1 |
| DATED | : May 14, 2002 | |
| INVENTOR(S) | : Pramod B. Mahajan, Jinrui Shi, Christopher Baszczynski, John McElver and Benjamin Bowen | |

It is certified that error appears in the above-identified patent and that said Letters Patent is hereby corrected as shown below:

<u>Title page, Item [54] and Column 1, line 3,</u>
The title should read -- [54] RecA HOMOLOGUES AND USES THEREOF --

Signed and Sealed this

Twenty-fourth Day of September, 2002

*Attest:*

JAMES E. ROGAN
*Attesting Officer*     *Director of the United States Patent and Trademark Office*

SEQUENCE LISTING

<160> NUMBER OF SEQ ID NOS: 10

<210> SEQ ID NO 1
<211> LENGTH: 1514
<212> TYPE: DNA
<213> ORGANISM: Zea mays
<220> FEATURE:
<221> NAME/KEY: CDS
<222> LOCATION: (46)...(1197)

<400> SEQUENCE: 1

| | | | | | |
|---|---|---|---|---|---|
| tcaaggcatt tgggcatctc acacttcttc gccttccttt aatgg atg act tat ctg | | | | | 57 |
| | | | | Met Thr Tyr Leu | |
| | | | | 1 | |
| ctt gaa ata tta tta tac ctt ttg aat ttt gac gca tta cga tgt tgc | | | | | 105 |
| Leu Glu Ile Leu Leu Tyr Leu Leu Asn Phe Asp Ala Leu Arg Cys Cys | | | | | |
| 5 | | 10 | | 15 | 20 |
| ttt ggt ttg tca cta aga gat att tat tca caa ttt cat ctg cag caa | | | | | 153 |
| Phe Gly Leu Ser Leu Arg Asp Ile Tyr Ser Gln Phe His Leu Gln Gln | | | | | |
| | | 25 | | 30 | 35 |
| aaa gtt ctt gat gcc gct atg aat gac ata aac aac tct ttt gga aaa | | | | | 201 |
| Lys Val Leu Asp Ala Ala Met Asn Asp Ile Asn Asn Ser Phe Gly Lys | | | | | |
| | 40 | | 45 | | 50 |
| gga agt gtt aca aga tta ggc agt gct ggt ggt gct ttt gtg gag aca | | | | | 249 |
| Gly Ser Val Thr Arg Leu Gly Ser Ala Gly Gly Ala Phe Val Glu Thr | | | | | |
| 55 | | | 60 | | 65 |
| ttc cca agt ggt tgt cta aca cta gat ttt gct ctg ggt ggc ggt ctt | | | | | 297 |
| Phe Pro Ser Gly Cys Leu Thr Leu Asp Phe Ala Leu Gly Gly Gly Leu | | | | | |
| 70 | | | 75 | | 80 |
| cca aaa gga aga gta gtg gag gta tat ggt cca gaa agc agt gga aag | | | | | 345 |
| Pro Lys Gly Arg Val Val Glu Val Tyr Gly Pro Glu Ser Ser Gly Lys | | | | | |
| 85 | | 90 | | 95 | 100 |
| act acc cta gct ttg cat gca att gct gaa ata cag aag ctt gga gga | | | | | 393 |
| Thr Thr Leu Ala Leu His Ala Ile Ala Glu Ile Gln Lys Leu Gly Gly | | | | | |
| | | 105 | | 110 | 115 |
| aat gcc atg ctt gtc gat gca gag cat gct ttt gat cca gct tat tca | | | | | 441 |
| Asn Ala Met Leu Val Asp Ala Glu His Ala Phe Asp Pro Ala Tyr Ser | | | | | |
| | 120 | | 125 | | 130 |
| aaa gct ctt ggg gta gat att gaa aat ctg att gtc tgc cag cct gac | | | | | 489 |
| Lys Ala Leu Gly Val Asp Ile Glu Asn Leu Ile Val Cys Gln Pro Asp | | | | | |
| | 135 | | 140 | | 145 |
| aac gga gag atg gca cta gaa att gcg gac cgt atg tgc aga tct gga | | | | | 537 |
| Asn Gly Glu Met Ala Leu Glu Ile Ala Asp Arg Met Cys Arg Ser Gly | | | | | |
| 150 | | | 155 | | 160 |
| gca ata gat ctt atc tgt att gat tcg gtg tca gcg ctc acc cca cgt | | | | | 585 |
| Ala Ile Asp Leu Ile Cys Ile Asp Ser Val Ser Ala Leu Thr Pro Arg | | | | | |
| 165 | | 170 | | 175 | 180 |
| gca gaa att gaa ggt gag ata gga atg cag cag atg ggt cta caa gct | | | | | 633 |
| Ala Glu Ile Glu Gly Glu Ile Gly Met Gln Gln Met Gly Leu Gln Ala | | | | | |
| | | 185 | | 190 | 195 |
| cgt ctg atg agt caa gca ttg aga aaa atg tca ggc aat gcc tca aag | | | | | 681 |
| Arg Leu Met Ser Gln Ala Leu Arg Lys Met Ser Gly Asn Ala Ser Lys | | | | | |
| | | 200 | | 205 | 210 |
| gct ggc tgt act ctt atg ttc ttg aat caa ata aga tac aag att gga | | | | | 729 |
| Ala Gly Cys Thr Leu Met Phe Leu Asn Gln Ile Arg Tyr Lys Ile Gly | | | | | |
| | 215 | | 220 | | 225 |
| gtg ttc tat ggg aat cct gaa gtc act agt gga ggg ata gcc ttg aaa | | | | | 777 |
| Val Phe Tyr Gly Asn Pro Glu Val Thr Ser Gly Gly Ile Ala Leu Lys | | | | | |
| | 230 | | 235 | | 240 |

-continued

| | |
|---|---|
| ttc ttt gca tct gtc cgt ctt gag ata cgg ctc att ggg aag ata aaa<br>Phe Phe Ala Ser Val Arg Leu Glu Ile Arg Leu Ile Gly Lys Ile Lys<br>245                                       250                         255                        260 | 825 |
| tct gcc aag gga gat gaa gat gtt ggt gtg aag gtt cgt gtc aga gtg<br>Ser Ala Lys Gly Asp Glu Asp Val Gly Val Lys Val Arg Val Arg Val<br>                       265                         270                         275 | 873 |
| cag aag agt aaa gta tct agg ccc tac aag caa gct gaa ttt gaa atc<br>Gln Lys Ser Lys Val Ser Arg Pro Tyr Lys Gln Ala Glu Phe Glu Ile<br>       280                       285                         290 | 921 |
| att ttt ggg gag ggt gtt agt aaa ttg ggg tgc gtt ctt gat tgt gct<br>Ile Phe Gly Glu Gly Val Ser Lys Leu Gly Cys Val Leu Asp Cys Ala<br>               295                       300                       305 | 969 |
| gag ctg atg gat gta gtt gca aag aag ggt tcg tgg tac agc tac aaa<br>Glu Leu Met Asp Val Val Ala Lys Lys Gly Ser Trp Tyr Ser Tyr Lys<br>310                                         315                         320 | 1017 |
| gat ata aga ttg ggc caa ggc aga gag aag gca ctg cag tat ctc cga<br>Asp Ile Arg Leu Gly Gln Gly Arg Glu Lys Ala Leu Gln Tyr Leu Arg<br>325                                       330                         335                         340 | 1065 |
| gag agc cca acc acc tgc gat gag ata gaa aag gtg gtt cga gct atg<br>Glu Ser Pro Thr Thr Cys Asp Glu Ile Glu Lys Val Val Arg Ala Met<br>                       345                         350                         355 | 1113 |
| ata cca gaa gga tcc aga cat atg agc cta cta gct ttc ggg cag tca<br>Ile Pro Glu Gly Ser Arg His Met Ser Leu Leu Ala Phe Gly Gln Ser<br>             360                       365                         370 | 1161 |
| tca tca act gaa gat gaa cag gcg tat gat gaa caa taatggtaca<br>Ser Ser Thr Glu Asp Glu Gln Ala Tyr Asp Glu Gln<br>       375                       380 | 1207 |
| tgaggttccg aagatggaac acttgtgaaa ccgtcaagct ctggcttgtg tcccttgcgg | 1267 |
| ataacagaaa agatcagagg taaccaacca atatggcagt tgtgtgagcg ctggagtgga | 1327 |
| gttgactaag accttgttcg tttctgccgg attggtgggt cctaacgatt cctgaccgga | 1387 |
| ttgtttctct aatttatata aactttgatt agctggaacg attccgggtg caatccgacg | 1447 |
| gaaatgaaca aggcctaatg ttgtacgtgt actgtggcat ggcagaaccg tccggtttaa | 1507 |
| cccaaaa | 1514 |

<210> SEQ ID NO 2
<211> LENGTH: 384
<212> TYPE: PRT
<213> ORGANISM: Zea mays

<400> SEQUENCE: 2

Met Thr Tyr Leu Leu Glu Ile Leu Leu Tyr Leu Leu Asn Phe Asp Ala
1                  5                        10                   15

Leu Arg Cys Cys Phe Gly Leu Ser Leu Arg Asp Ile Tyr Ser Gln Phe
                 20                     25                     30

His Leu Gln Gln Lys Val Leu Asp Ala Ala Met Asn Asp Ile Asn Asn
               35                     40                     45

Ser Phe Gly Lys Gly Ser Val Thr Arg Leu Gly Ser Ala Gly Gly Ala
   50                     55                     60

Phe Val Glu Thr Phe Pro Ser Gly Cys Leu Thr Leu Asp Phe Ala Leu
65                  70                     75                     80

Gly Gly Gly Leu Pro Lys Gly Arg Val Val Glu Val Tyr Gly Pro Glu
                 85                     90                     95

Ser Ser Gly Lys Thr Thr Leu Ala Leu His Ala Ile Ala Glu Ile Gln
              100                   105                   110

Lys Leu Gly Gly Asn Ala Met Leu Val Asp Ala Glu His Ala Phe Asp
         115                   120                   125

```
Pro Ala Tyr Ser Lys Ala Leu Gly Val Asp Ile Glu Asn Leu Ile Val
    130                 135                 140

Cys Gln Pro Asp Asn Gly Glu Met Ala Leu Glu Ile Ala Asp Arg Met
145                 150                 155                 160

Cys Arg Ser Gly Ala Ile Asp Leu Ile Cys Ile Asp Ser Val Ser Ala
                165                 170                 175

Leu Thr Pro Arg Ala Glu Ile Glu Gly Glu Ile Gly Met Gln Gln Met
            180                 185                 190

Gly Leu Gln Ala Arg Leu Met Ser Gln Ala Leu Arg Lys Met Ser Gly
        195                 200                 205

Asn Ala Ser Lys Ala Gly Cys Thr Leu Met Phe Leu Asn Gln Ile Arg
    210                 215                 220

Tyr Lys Ile Gly Val Phe Tyr Gly Asn Pro Glu Val Thr Ser Gly Gly
225                 230                 235                 240

Ile Ala Leu Lys Phe Phe Ala Ser Val Arg Leu Glu Ile Arg Leu Ile
                245                 250                 255

Gly Lys Ile Lys Ser Ala Lys Gly Asp Glu Asp Val Gly Val Lys Val
            260                 265                 270

Arg Val Arg Val Gln Lys Ser Lys Val Ser Arg Pro Tyr Lys Gln Ala
        275                 280                 285

Glu Phe Glu Ile Ile Phe Gly Glu Gly Val Ser Lys Leu Gly Cys Val
    290                 295                 300

Leu Asp Cys Ala Glu Leu Met Asp Val Val Ala Lys Lys Gly Ser Trp
305                 310                 315                 320

Tyr Ser Tyr Lys Asp Ile Arg Leu Gly Gln Gly Arg Glu Lys Ala Leu
                325                 330                 335

Gln Tyr Leu Arg Glu Ser Pro Thr Thr Cys Asp Glu Ile Glu Lys Val
            340                 345                 350

Val Arg Ala Met Ile Pro Glu Gly Ser Arg His Met Ser Leu Leu Ala
        355                 360                 365

Phe Gly Gln Ser Ser Ser Thr Glu Asp Glu Gln Ala Tyr Asp Glu Gln
    370                 375                 380

<210> SEQ ID NO 3
<211> LENGTH: 1545
<212> TYPE: DNA
<213> ORGANISM: Zea mays
<220> FEATURE:
<221> NAME/KEY: CDS
<222> LOCATION: (136)...(1362)

<400> SEQUENCE: 3
gcccgccatt ctgaattgga ccgacccacg catgcctcgc tacgtagaga agactcggtg      60
acgtgggccc acccatccac cacaccactc gagcgcgcgc gcggcccacc gctccgccgc     120
tgcccgcccg ccgcc atg cga ggg atc ctc tcc tct tcc tcc gct ctc ctc     171
               Met Arg Gly Ile Leu Ser Ser Ser Ser Ala Leu Leu
                 1               5                  10 cgg cga gcc ggc gcc cag ctc tcg cgc acg gac tgc agt agc ccc tca     219
Arg Arg Ala Gly Ala Gln Leu Ser Arg Thr Asp Cys Ser Ser Pro Ser
        15                  20                  25 gcg tcc gcg acc tct cct ctc cgc cgc tcc cct ctt cag aat ggg aaa     267
Ala Ser Ala Thr Ser Pro Leu Arg Arg Ser Pro Leu Gln Asn Gly Lys
    30                  35                  40 aga gac aca ttt tgt tcg ctt tgg ttc aaa ggt cgt tcg gta tca acc     315
Arg Asp Thr Phe Cys Ser Leu Trp Phe Lys Gly Arg Ser Val Ser Thr
45                  50                  55                  60
```

-continued

| | | |
|---|---|---|
| aca gtt gat atg cag tta gac tat gag agt gat ccc cct ctt gac gat<br>Thr Val Asp Met Gln Leu Asp Tyr Glu Ser Asp Pro Pro Leu Asp Asp<br>                  65                      70                    75 | | 363 |
| aca aaa gct att gag aag gag tca tca ctt aat gtt gct gtt tct caa<br>Thr Lys Ala Ile Glu Lys Glu Ser Ser Leu Asn Val Ala Val Ser Gln<br>              80                      85                    90 | | 411 |
| ctc gca att gac ttc gat aga gac tct aat tta tgt ttg gag cga ttt<br>Leu Ala Ile Asp Phe Asp Arg Asp Ser Asn Leu Cys Leu Glu Arg Phe<br>        95                      100                  105 | | 459 |
| tcc cgt gca agg aaa gca tct gta gtc tct act ggt tct ctt aag ctt<br>Ser Arg Ala Arg Lys Ala Ser Val Val Ser Thr Gly Ser Leu Lys Leu<br>110                      115                    120 | | 507 |
| gac ctc gct ctc ggc gtt gga gga tta ccg aag ggt aga atg gtg gag<br>Asp Leu Ala Leu Gly Val Gly Gly Leu Pro Lys Gly Arg Met Val Glu<br>125                      130                    135                    140 | | 555 |
| ata tat ggg aaa gaa gca tct ggg aag aca aca ctc gcg ctt cat gtt<br>Ile Tyr Gly Lys Glu Ala Ser Gly Lys Thr Thr Leu Ala Leu His Val<br>                    145                    150                    155 | | 603 |
| att aag gaa gct caa aag aat gga ggt tat tgt gct tat att gat gca<br>Ile Lys Glu Ala Gln Lys Asn Gly Gly Tyr Cys Ala Tyr Ile Asp Ala<br>              160                      165                    170 | | 651 |
| gaa aat gcc ttc aac cct tca ttt gct gaa tct att ggc gta gac agt<br>Glu Asn Ala Phe Asn Pro Ser Phe Ala Glu Ser Ile Gly Val Asp Ser<br>175                      180                    185 | | 699 |
| gaa agg ctc ttg ata gcc caa cct gat tct gct gaa aat tct cta agc<br>Glu Arg Leu Leu Ile Ala Gln Pro Asp Ser Ala Glu Asn Ser Leu Ser<br>        190                      195                  200 | | 747 |
| att gta aac act ctt gtt ggt ggt tct gtt gct gtt gtt gtt gtg gac<br>Ile Val Asn Thr Leu Val Gly Gly Ser Val Ala Val Val Val Val Asp<br>205                      210                    215                    220 | | 795 |
| agt gtg gca gca ctt att ccc aaa tgt gaa att gaa ggt gaa ata tac<br>Ser Val Ala Ala Leu Ile Pro Lys Cys Glu Ile Glu Gly Glu Ile Tyr<br>                    225                    230                    235 | | 843 |
| aca aat tgt gga gac atc caa tcc cat ttg atg act cgg gcc ctt aga<br>Thr Asn Cys Gly Asp Ile Gln Ser His Leu Met Thr Arg Ala Leu Arg<br>              240                      245                    250 | | 891 |
| aaa att cag tac act tta tgt cga tct gaa aca ctt att att ttt gtg<br>Lys Ile Gln Tyr Thr Leu Cys Arg Ser Glu Thr Leu Ile Ile Phe Val<br>        255                      260                  265 | | 939 |
| aat cag gtt aga aca aag cgg aca tca agt aat cct ggg atc tac aag<br>Asn Gln Val Arg Thr Lys Arg Thr Ser Ser Asn Pro Gly Ile Tyr Lys<br>270                      275                    280 | | 987 |
| gag gtg cct tgc ggt ggt aat gca cta gga ttc tat gct gca gtc aga<br>Glu Val Pro Cys Gly Gly Asn Ala Leu Gly Phe Tyr Ala Ala Val Arg<br>285                      290                    295                    300 | | 1035 |
| atg agg act tca agg aga gaa ctg cgc tat agt gaa gat gag gct acc<br>Met Arg Thr Ser Arg Arg Glu Leu Arg Tyr Ser Glu Asp Glu Ala Thr<br>                    305                    310                    315 | | 1083 |
| ggc gta ggt ata tca gtg cag atc atc aag aac aaa ttg gct cca gcg<br>Gly Val Gly Ile Ser Val Gln Ile Ile Lys Asn Lys Leu Ala Pro Ala<br>              320                      325                    330 | | 1131 |
| aac ctg aag aag gaa gcc ggc atc gac atc aca ttc ggt aag ggg atc<br>Asn Leu Lys Lys Glu Ala Gly Ile Asp Ile Thr Phe Gly Lys Gly Ile<br>        335                      340                  345 | | 1179 |
| tgc cac gag tcg gag atc ctg gag acg gct tcc tcc gtc gga gtg atc<br>Cys His Glu Ser Glu Ile Leu Glu Thr Ala Ser Ser Val Gly Val Ile<br>350                      355                    360 | | 1227 |
| ctg aaa gac ggg tgt ggg tat tgg atc aac aac gag ttc ctg gca ggc<br>Leu Lys Asp Gly Cys Gly Tyr Trp Ile Asn Asn Glu Phe Leu Ala Gly | | 1275 |

-continued

```
        365                 370                 375                 380
aag gtg gaa gcg gag aag ttc ctg cgt gaa aac gct gca gtg gca gat     1323
Lys Val Glu Ala Glu Lys Phe Leu Arg Glu Asn Ala Ala Val Ala Asp
                    385                 390                 395 gag atc tgc aat acc gtg agg aac gag ttc ttg caa agg tgacataggg      1372
Glu Ile Cys Asn Thr Val Arg Asn Glu Phe Leu Gln Arg
                400                 405 cgaccgatta gagaggctaa tgcattagtt agtcggaaat gttgtaccgt catgtattca   1432
tagaagaaga tttatgtagg atgttgctgt gcctgtcgtg taactttgac tcgcaacagt   1492
tcattgagtt taccagggcc attccctccc agatcaaaaa aaaaaaaaaa aaa          1545

<210> SEQ ID NO 4
<211> LENGTH: 409
<212> TYPE: PRT
<213> ORGANISM: Zea mays

<400> SEQUENCE: 4

Met Arg Gly Ile Leu Ser Ser Ser Ala Leu Leu Arg Arg Ala Gly
 1               5                  10                  15

Ala Gln Leu Ser Arg Thr Asp Cys Ser Ser Pro Ser Ala Ser Ala Thr
                20                  25                  30

Ser Pro Leu Arg Arg Ser Pro Leu Gln Asn Gly Lys Arg Asp Thr Phe
            35                  40                  45

Cys Ser Leu Trp Phe Lys Gly Arg Ser Val Ser Thr Thr Val Asp Met
 50                  55                  60

Gln Leu Asp Tyr Glu Ser Asp Pro Pro Leu Asp Asp Thr Lys Ala Ile
 65                  70                  75                  80

Glu Lys Glu Ser Ser Leu Asn Val Ala Val Ser Gln Leu Ala Ile Asp
                85                  90                  95

Phe Asp Arg Asp Ser Asn Leu Cys Leu Glu Arg Phe Ser Arg Ala Arg
                100                 105                 110

Lys Ala Ser Val Val Ser Thr Gly Ser Leu Lys Leu Asp Leu Ala Leu
            115                 120                 125

Gly Val Gly Gly Leu Pro Lys Gly Arg Met Val Glu Ile Tyr Gly Lys
        130                 135                 140

Glu Ala Ser Gly Lys Thr Thr Leu Ala Leu His Val Ile Lys Glu Ala
145                 150                 155                 160

Gln Lys Asn Gly Gly Tyr Cys Ala Tyr Ile Asp Ala Glu Asn Ala Phe
                165                 170                 175

Asn Pro Ser Phe Ala Glu Ser Ile Gly Val Asp Ser Glu Arg Leu Leu
            180                 185                 190

Ile Ala Gln Pro Asp Ser Ala Glu Asn Ser Leu Ser Ile Val Asn Thr
        195                 200                 205

Leu Val Gly Gly Ser Val Ala Val Val Val Asp Ser Val Ala Ala
    210                 215                 220

Leu Ile Pro Lys Cys Glu Ile Glu Gly Glu Ile Tyr Thr Asn Cys Gly
225                 230                 235                 240

Asp Ile Gln Ser His Leu Met Thr Arg Ala Leu Arg Lys Ile Gln Tyr
                245                 250                 255

Thr Leu Cys Arg Ser Glu Thr Leu Ile Ile Phe Val Asn Gln Val Arg
            260                 265                 270

Thr Lys Arg Thr Ser Ser Asn Pro Gly Ile Tyr Lys Glu Val Pro Cys
        275                 280                 285

Gly Gly Asn Ala Leu Gly Phe Tyr Ala Ala Val Arg Met Arg Thr Ser
```

|   |   |   |   |   |   |   |   |   |   |   |
|---|---|---|---|---|---|---|---|---|---|---|
|   | 290 |   |   |   | 295 |   |   |   | 300 |   |
| Arg | Arg | Glu | Leu | Arg | Tyr | Ser | Glu | Asp | Glu | Ala | Thr | Gly | Val | Gly | Ile |
| 305 |   |   |   |   | 310 |   |   |   | 315 |   |   |   |   | 320 |   |
| Ser | Val | Gln | Ile | Ile | Lys | Asn | Lys | Leu | Ala | Pro | Ala | Asn | Leu | Lys | Lys |
|   |   |   |   | 325 |   |   |   |   | 330 |   |   |   |   | 335 |   |
| Glu | Ala | Gly | Ile | Asp | Ile | Thr | Phe | Gly | Lys | Gly | Ile | Cys | His | Glu | Ser |
|   |   |   | 340 |   |   |   |   | 345 |   |   |   |   | 350 |   |   |
| Glu | Ile | Leu | Glu | Thr | Ala | Ser | Ser | Val | Gly | Val | Ile | Leu | Lys | Asp | Gly |
|   |   | 355 |   |   |   |   | 360 |   |   |   |   | 365 |   |   |   |
| Cys | Gly | Tyr | Trp | Ile | Asn | Asn | Glu | Phe | Leu | Ala | Gly | Lys | Val | Glu | Ala |
|   | 370 |   |   |   |   | 375 |   |   |   |   | 380 |   |   |   |   |
| Glu | Lys | Phe | Leu | Arg | Glu | Asn | Ala | Ala | Val | Ala | Asp | Glu | Ile | Cys | Asn |
| 385 |   |   |   |   | 390 |   |   |   |   | 395 |   |   |   |   | 400 |
| Thr | Val | Arg | Asn | Glu | Phe | Leu | Gln | Arg |   |   |   |   |   |   |   |
|   |   |   |   | 405 |   |   |   |   |   |   |   |   |   |   |   |

<210> SEQ ID NO 5
<211> LENGTH: 1828
<212> TYPE: DNA
<213> ORGANISM: Zea mays
<220> FEATURE:
<221> NAME/KEY: CDS
<222> LOCATION: (100)...(1389)

<400> SEQUENCE: 5

```
gaattcccgg gtcgacccac gcgtccgaaa cccctaaacc ctagctcccc accccagcc      60 tccccgcggc ttccagcgat tggaggcgaa gcagccgcc atg gcg atc ctc ctt     114
                                            Met Ala Ile Leu Leu
                                              1               5 agg cgc gcg tcg ctg cgg cgc gtc atc gcc ttc gcc gcc gcc tcc tcc     162
Arg Arg Ala Ser Leu Arg Arg Val Ile Ala Phe Ala Ala Ala Ser Ser
             10                  15                  20 tcc tcc tct tct ttg cac tct gag att tat aag caa ggg gtt tgt gga     210
Ser Ser Ser Ser Leu His Ser Glu Ile Tyr Lys Gln Gly Val Cys Gly
         25                  30                  35 tcc atg ttt cat tgc cga gag ttc gca tca aaa gcc aaa aaa aag aag     258
Ser Met Phe His Cys Arg Glu Phe Ala Ser Lys Ala Lys Lys Lys Lys
     40                  45                  50 tca agt gga aca gac tcc gat gag gag agt atg tca aag aaa gac ttg     306
Ser Ser Gly Thr Asp Ser Asp Glu Glu Ser Met Ser Lys Lys Asp Leu
 55                  60                  65 gct tta cac cag gct atc gat caa ata acg tct gca ttt ggg aag ggg     354
Ala Leu His Gln Ala Ile Asp Gln Ile Thr Ser Ala Phe Gly Lys Gly
         70                  75                  80                  85 gca ata atg tgg ctt ggg cgt tcg caa ggc ctt aga gat gta cct gtt     402
Ala Ile Met Trp Leu Gly Arg Ser Gln Gly Leu Arg Asp Val Pro Val
             90                  95                 100 gtg tct act ggg tct ttc gct ttg gat atg gct cta gga act ggt ggt     450
Val Ser Thr Gly Ser Phe Ala Leu Asp Met Ala Leu Gly Thr Gly Gly
        105                 110                 115 ctt cca aag ggg cgt gtc ata gag gtc tat ggt cca gag gct tca ggc     498
Leu Pro Lys Gly Arg Val Ile Glu Val Tyr Gly Pro Glu Ala Ser Gly
    120                 125                 130 aag aca aca ctt gct cta cat gtc att gca gaa gca caa aag aat ggg     546
Lys Thr Thr Leu Ala Leu His Val Ile Ala Glu Ala Gln Lys Asn Gly
135                 140                 145 ggt tac tgt gcc ttt gta gat gca gaa cac gct ttg gat cca gct ctt     594
Gly Tyr Cys Ala Phe Val Asp Ala Glu His Ala Leu Asp Pro Ala Leu
150                 155                 160                 165
```

```
gca gag tca att ggt gtt gac act aac aat ttg ctc gtc tct cag cca    642
Ala Glu Ser Ile Gly Val Asp Thr Asn Asn Leu Leu Val Ser Gln Pro
            170                 175                 180 gac tgc gct gag caa gca ctc agt ctt gtg gac aca ctg att cga agt    690
Asp Cys Ala Glu Gln Ala Leu Ser Leu Val Asp Thr Leu Ile Arg Ser
            185                 190                 195 gga tct gtt gat gtt gtt gta gta gac agt gta gct gcg ctt gtt cca    738
Gly Ser Val Asp Val Val Val Val Asp Ser Val Ala Ala Leu Val Pro
            200                 205                 210 aag act gag ctt gat ggt gag atg ggt gat gca cat gtt gct ctt cag    786
Lys Thr Glu Leu Asp Gly Glu Met Gly Asp Ala His Val Ala Leu Gln
            215                 220                 225 gct agg ttg atg agc caa gct ctt cgc aag ctt agc cac tca ctt tca    834
Ala Arg Leu Met Ser Gln Ala Leu Arg Lys Leu Ser His Ser Leu Ser
230                 235                 240                 245 ctt tcg cag aca gtt ttg tta ttt att aat cag atc agg gcc aag gta    882
Leu Ser Gln Thr Val Leu Leu Phe Ile Asn Gln Ile Arg Ala Lys Val
            250                 255                 260 gcc aca ttt gga ttt gga gga cca act gag gtc act tct ggt ggt aac    930
Ala Thr Phe Gly Phe Gly Gly Pro Thr Glu Val Thr Ser Gly Gly Asn
            265                 270                 275 gcc ttg aag ttt tat gct tct gtt cgc ttg aac atc agg cgt att ggt    978
Ala Leu Lys Phe Tyr Ala Ser Val Arg Leu Asn Ile Arg Arg Ile Gly
            280                 285                 290 ttt tta aag gaa ggt gaa gag aca ata ggt agt cag gtt gct gtg aag    1026
Phe Leu Lys Glu Gly Glu Glu Thr Ile Gly Ser Gln Val Ala Val Lys
            295                 300                 305 att gta aaa aat aag cat gcc cca ccc ttc aag act gca cag ttt gag    1074
Ile Val Lys Asn Lys His Ala Pro Pro Phe Lys Thr Ala Gln Phe Glu
310                 315                 320                 325 ctt gaa ttt gga aag ggg ata tgc cgc agt tct gag ctt ttt gaa ctt    1122
Leu Glu Phe Gly Lys Gly Ile Cys Arg Ser Ser Glu Leu Phe Glu Leu
            330                 335                 340 ggg ttg aag cac aag ctt atc caa aag act ggc ggt gca tat tat aga    1170
Gly Leu Lys His Lys Leu Ile Gln Lys Thr Gly Gly Ala Tyr Tyr Arg
            345                 350                 355 ttc aat gat atg agt ttc aaa ggt aaa aat aac ctt aaa tct tac ctt    1218
Phe Asn Asp Met Ser Phe Lys Gly Lys Asn Asn Leu Lys Ser Tyr Leu
            360                 365                 370 act gaa aac aag agt gtt gca aat gat ctg gag acg aaa cta agg aga    1266
Thr Glu Asn Lys Ser Val Ala Asn Asp Leu Glu Thr Lys Leu Arg Arg
375                 380                 385 ttg atg gga acc gaa gca cct aaa gag cag gag gca gaa gac agt tcg    1314
Leu Met Gly Thr Glu Ala Pro Lys Glu Gln Glu Ala Glu Asp Ser Ser
390                 395                 400                 405 ccg agt gat ttg cct gaa gag gtt gtc aca cct gaa gca tcc tca gaa    1362
Pro Ser Asp Leu Pro Glu Glu Val Val Thr Pro Glu Ala Ser Ser Glu
            410                 415                 420 gag gat atg gga gtc gta atc gag gct tgaccagtga tctgacgtgc          1409
Glu Asp Met Gly Val Val Ile Glu Ala
            425                 430 tggcaagcga gaccagaatt tctggagctg ttcctgtaaa acaatatttt gggtcctgaa  1469
gtcaccaccg cttggatcga catgaccctg cggtgttctg gtgattccat tgtaacagac  1529
ttcagccctt accgtgcttt tacagtagtg tagcatgaag agaattggca ttgtgtgaaa  1589
tcatgctgat agctgagagg tggaagttga aggcggtaag gttgtggtct ctggctatct  1649
gaactctagt gtagtatata gtgtaggcga cggtaaaatg tagtggcgtg gtcgtgtata  1709
```

```
catgatgctc acattttgag ctcctggttt cacgtcgaag ccaatttcaa aagcattctt    1769
tattgagcgc agctagaatt acatcgaaaa aaaaaaaaaa aaaaaaaaaa aaaaaaaa      1828
```

<210> SEQ ID NO 6
<211> LENGTH: 430
<212> TYPE: PRT
<213> ORGANISM: Zea mays

<400> SEQUENCE: 6

```
Met Ala Ile Leu Leu Arg Arg Ala Ser Leu Arg Arg Val Ile Ala Phe
 1               5                  10                  15

Ala Ala Ala Ser Ser Ser Ser Ser Leu His Ser Glu Ile Tyr Lys
            20                  25                  30

Gln Gly Val Cys Gly Ser Met Phe His Cys Arg Glu Phe Ala Ser Lys
        35                  40                  45

Ala Lys Lys Lys Ser Ser Gly Thr Asp Ser Asp Glu Glu Ser Met
 50                  55                  60

Ser Lys Lys Asp Leu Ala Leu His Gln Ala Ile Asp Gln Ile Thr Ser
 65                  70                  75                  80

Ala Phe Gly Lys Gly Ala Ile Met Trp Leu Gly Arg Ser Gln Gly Leu
                85                  90                  95

Arg Asp Val Pro Val Val Ser Thr Gly Ser Phe Ala Leu Asp Met Ala
            100                 105                 110

Leu Gly Thr Gly Gly Leu Pro Lys Gly Arg Val Ile Glu Val Tyr Gly
        115                 120                 125

Pro Glu Ala Ser Gly Lys Thr Thr Leu Ala Leu His Val Ile Ala Glu
    130                 135                 140

Ala Gln Lys Asn Gly Gly Tyr Cys Ala Phe Val Asp Ala Glu His Ala
145                 150                 155                 160

Leu Asp Pro Ala Leu Ala Glu Ser Ile Gly Val Asp Thr Asn Asn Leu
                165                 170                 175

Leu Val Ser Gln Pro Asp Cys Ala Glu Gln Ala Leu Ser Leu Val Asp
            180                 185                 190

Thr Leu Ile Arg Ser Gly Ser Val Asp Val Val Val Asp Ser Val
        195                 200                 205

Ala Ala Leu Val Pro Lys Thr Glu Leu Asp Gly Glu Met Gly Asp Ala
    210                 215                 220

His Val Ala Leu Gln Ala Arg Leu Met Ser Gln Ala Leu Arg Lys Leu
225                 230                 235                 240

Ser His Ser Leu Ser Leu Ser Gln Thr Val Leu Leu Phe Ile Asn Gln
                245                 250                 255

Ile Arg Ala Lys Val Ala Thr Phe Gly Phe Gly Pro Thr Glu Val
            260                 265                 270

Thr Ser Gly Gly Asn Ala Leu Lys Phe Tyr Ala Ser Val Arg Leu Asn
        275                 280                 285

Ile Arg Arg Ile Gly Phe Leu Lys Glu Gly Glu Thr Ile Gly Ser
    290                 295                 300

Gln Val Ala Val Lys Ile Val Lys Asn Lys His Ala Pro Pro Phe Lys
305                 310                 315                 320

Thr Ala Gln Phe Glu Leu Glu Phe Gly Lys Gly Ile Cys Arg Ser Ser
                325                 330                 335

Glu Leu Phe Glu Leu Gly Leu Lys His Lys Leu Ile Gln Lys Thr Gly
            340                 345                 350

Gly Ala Tyr Tyr Arg Phe Asn Asp Met Ser Phe Lys Gly Lys Asn Asn
```

```
                   355                 360                 365
Leu Lys Ser Tyr Leu Thr Glu Asn Lys Ser Val Ala Asn Asp Leu Glu
        370                 375                 380

Thr Lys Leu Arg Arg Leu Met Gly Thr Glu Ala Pro Lys Glu Gln Glu
385                 390                 395                 400

Ala Glu Asp Ser Ser Pro Ser Asp Leu Pro Glu Glu Val Val Thr Pro
                405                 410                 415

Glu Ala Ser Ser Glu Glu Asp Met Gly Val Val Ile Glu Ala
            420                 425                 430

<210> SEQ ID NO 7
<211> LENGTH: 1773
<212> TYPE: DNA
<213> ORGANISM: Zea mays
<220> FEATURE:
<221> NAME/KEY: CDS
<222> LOCATION: (97)...(1371)

<400> SEQUENCE: 7
aattcggcac gagaaaaccc ctaaacccta gccctcacc  tctcgcctcc gccctcatcc      60
gcgcgacttg cagcggttgg aggcgaagcc ggctcc atg acg acc ctc ctc agg       114
                                        Met Thr Thr Leu Leu Arg
                                          1               5 cgc gcg tcg ctg cgg cgc gtc att gcc gcc gcc gcc gcc tct tct ttt      162
Arg Ala Ser Leu Arg Arg Val Ile Ala Ala Ala Ala Ala Ser Ser Phe
              10                  15                  20 cac cct gag agc tat aag caa ggg atc tgt ggc tcc aca ttt cat tgc      210
His Pro Glu Ser Tyr Lys Gln Gly Ile Cys Gly Ser Thr Phe His Cys
         25                  30                  35 cga gag ttc gca tca aaa gca aaa aag aag tca agt gga aca gac tct      258
Arg Glu Phe Ala Ser Lys Ala Lys Lys Lys Ser Ser Gly Thr Asp Ser
     40                  45                  50 ggg gag gag aac atg tca aag aaa gac ttg gct tta cac cag gct att      306
Gly Glu Glu Asn Met Ser Lys Lys Asp Leu Ala Leu His Gln Ala Ile
 55                  60                  65                  70 gat cag ata acg tct gca ttt ggg aag ggg gca ata atg tgg ctt ggg      354
Asp Gln Ile Thr Ser Ala Phe Gly Lys Gly Ala Ile Met Trp Leu Gly
                 75                  80                  85 cgt tca caa ggc cat aga gat gta cca gtc gtg tct act ggg tct ttg      402
Arg Ser Gln Gly His Arg Asp Val Pro Val Val Ser Thr Gly Ser Leu
             90                  95                 100 gat ttg gat atg gct cta gga act ggt ggt ctt cca aag ggg cgt gtt      450
Asp Leu Asp Met Ala Leu Gly Thr Gly Gly Leu Pro Lys Gly Arg Val
        105                 110                 115 gta gag gta tat ggt cca gag gca tca ggc aag aca acg ctt gct cta      498
Val Glu Val Tyr Gly Pro Glu Ala Ser Gly Lys Thr Thr Leu Ala Leu
    120                 125                 130 cat gtc att gca gaa gca caa aag aat gga ggt tac tgt gcc ttt gta      546
His Val Ile Ala Glu Ala Gln Lys Asn Gly Gly Tyr Cys Ala Phe Val
135                 140                 145                 150 gat gca gag cac gct ttg gat cca gct ctc gcc gag tca att ggt gtt      594
Asp Ala Glu His Ala Leu Asp Pro Ala Leu Ala Glu Ser Ile Gly Val
                155                 160                 165 gac act aac aat tta ctc ctt tct cag ccc gat tgt gct gag cag gca      642
Asp Thr Asn Asn Leu Leu Leu Ser Gln Pro Asp Cys Ala Glu Gln Ala
            170                 175                 180 ctc agt ctt gtg gac aca ctg att cga agt gga tct gtt gat gtt gtt      690
Leu Ser Leu Val Asp Thr Leu Ile Arg Ser Gly Ser Val Asp Val Val
        185                 190                 195
```

```
gta gta gac agt gtt gct gcg ctt gtt cca aag act gag ctt gat ggt       738
Val Val Asp Ser Val Ala Ala Leu Val Pro Lys Thr Glu Leu Asp Gly
    200                 205                 210 gag atg ggt gat gca cat gtt gct ctt cag gct agg ttg atg agt caa       786
Glu Met Gly Asp Ala His Val Ala Leu Gln Ala Arg Leu Met Ser Gln
215                 220                 225                 230 gcc ctt cgc aag ctt agc cac tcc ctt tca ctt tcg caa aca att ttg       834
Ala Leu Arg Lys Leu Ser His Ser Leu Ser Leu Ser Gln Thr Ile Leu
                235                 240                 245 tta ttt att aat cag atc agg gcc aag gta gcc aca ttt gga ttt gga       882
Leu Phe Ile Asn Gln Ile Arg Ala Lys Val Ala Thr Phe Gly Phe Gly
        250                 255                 260 gga cca act gag gtt act tct ggt ggc aac gcc ttg aag ttt tat gcg       930
Gly Pro Thr Glu Val Thr Ser Gly Gly Asn Ala Leu Lys Phe Tyr Ala
            265                 270                 275 tct gtt cgc ttg aac atc agg cgt att ggt ttg gta aag aaa ggc gaa       978
Ser Val Arg Leu Asn Ile Arg Arg Ile Gly Leu Val Lys Lys Gly Glu
                280                 285                 290 gag aca ata ggt agt cag att gct gtg aag att gta aaa aac aag cat      1026
Glu Thr Ile Gly Ser Gln Ile Ala Val Lys Ile Val Lys Asn Lys His
295                 300                 305                 310 gcc cca ccc ttc aag act gca cag ttt gag ctt gaa ttt gga aag ggg      1074
Ala Pro Pro Phe Lys Thr Ala Gln Phe Glu Leu Glu Phe Gly Lys Gly
                315                 320                 325 ata tgc cgc agt tct gag ctt ttt gaa ctt gga ttg aag cat aag ctt      1122
Ile Cys Arg Ser Ser Glu Leu Phe Glu Leu Gly Leu Lys His Lys Leu
            330                 335                 340 atc cga aag agt ggt ggt tca tat tat agt ttc aat ggt aag gct ttc      1170
Ile Arg Lys Ser Gly Gly Ser Tyr Tyr Ser Phe Asn Gly Lys Ala Phe
        345                 350                 355 aat ggt aaa agt aac ctt aaa tct tac ctt act gaa aac aag agc gtt      1218
Asn Gly Lys Ser Asn Leu Lys Ser Tyr Leu Thr Glu Asn Lys Ser Val
    360                 365                 370 gca aat gat ctg gag atg gaa cta aag aga ttg atg gga act gat gcg      1266
Ala Asn Asp Leu Glu Met Glu Leu Lys Arg Leu Met Gly Thr Asp Ala
375                 380                 385                 390 tct aaa gag cag gag gca gga gac agt tcg cag agt gat ttg cct gaa      1314
Ser Lys Glu Gln Glu Ala Gly Asp Ser Ser Gln Ser Asp Leu Pro Glu
                395                 400                 405 gag agt gtc aca cct gaa gca tcg tca gaa gag gat ctg gga gcc ata      1362
Glu Ser Val Thr Pro Glu Ala Ser Ser Glu Glu Asp Leu Gly Ala Ile
            410                 415                 420 att gaa ggt tagccagtga tctgatgtgc tggcaagtgg gaacagaatt              1411
Ile Glu Gly
        425 tctggactct ggagcagttg ttcctgtaaa acaatatctt gggtcctgaa gtcaccaccg    1471 tttggatcga catgccctgt ggtgttctgg tgatctcatc gtagcagact tcagtcttta    1531 ctgtgcttat acagtagtgc agcaggaaga gaattcacat tgtgtgaaat catggtgata    1591 gctgagaggt ggaagttgaa gtaagccggg aagggtgagg tattgtggtc cgtgccattt    1651 aaacttcagt aagcaaacgt cgtgtatata tgatgtgcac atttttaaaac ggggcattct   1711 ttattgactg ctgcttagat ttacattgag ctccctccac ttccaaaaaa aaaaaaaaa    1771 aa                                                                   1773

<210> SEQ ID NO 8
<211> LENGTH: 425
<212> TYPE: PRT
<213> ORGANISM: Zea mays
```

<400> SEQUENCE: 8

| | | | | | | | | | | | | | | | |
|---|---|---|---|---|---|---|---|---|---|---|---|---|---|---|---|
|Met|Thr|Thr|Leu|Leu|Arg|Arg|Ala|Ser|Leu|Arg|Arg|Val|Ile|Ala|Ala|
|1| | | |5| | | | |10| | | | |15| |
|Ala|Ala|Ala|Ser|Ser|Phe|His|Pro|Glu|Ser|Tyr|Lys|Gln|Gly|Ile|Cys|
| | | |20| | | |25| | | |30| | | | |
|Gly|Ser|Thr|Phe|His|Cys|Arg|Glu|Phe|Ala|Ser|Lys|Ala|Lys|Lys|Lys|
| | |35| | | | |40| | | |45| | | | |
|Ser|Ser|Gly|Thr|Asp|Ser|Gly|Glu|Glu|Asn|Met|Ser|Lys|Lys|Asp|Leu|
| |50| | | | |55| | | |60| | | | | |
|Ala|Leu|His|Gln|Ala|Ile|Asp|Gln|Ile|Thr|Ser|Ala|Phe|Gly|Lys|Gly|
|65| | | | |70| | | | |75| | | | |80|
|Ala|Ile|Met|Trp|Leu|Gly|Arg|Ser|Gln|Gly|His|Arg|Asp|Val|Pro|Val|
| | | | |85| | | | |90| | | | |95| |
|Val|Ser|Thr|Gly|Ser|Leu|Asp|Leu|Asp|Met|Ala|Leu|Gly|Thr|Gly|Gly|
| | | |100| | | | |105| | | | |110| | |
|Leu|Pro|Lys|Gly|Arg|Val|Val|Glu|Val|Tyr|Gly|Pro|Glu|Ala|Ser|Gly|
| | | |115| | | | |120| | | | |125| | |
|Lys|Thr|Thr|Leu|Ala|Leu|His|Val|Ile|Ala|Glu|Ala|Gln|Lys|Asn|Gly|
| | |130| | | | |135| | | | |140| | | |
|Gly|Tyr|Cys|Ala|Phe|Val|Asp|Ala|Glu|His|Ala|Leu|Asp|Pro|Ala|Leu|
|145| | | | |150| | | | |155| | | | |160|
|Ala|Glu|Ser|Ile|Gly|Val|Asp|Thr|Asn|Asn|Leu|Leu|Leu|Ser|Gln|Pro|
| | | |165| | | | |170| | | | |175| | |
|Asp|Cys|Ala|Glu|Gln|Ala|Leu|Ser|Leu|Val|Asp|Thr|Leu|Ile|Arg|Ser|
| | | |180| | | | |185| | | | |190| | |
|Gly|Ser|Val|Asp|Val|Val|Val|Asp|Ser|Val|Ala|Ala|Leu|Val|Pro|
| | | |195| | | | |200| | | | |205| | |
|Lys|Thr|Glu|Leu|Asp|Gly|Glu|Met|Gly|Asp|Ala|His|Val|Ala|Leu|Gln|
| | |210| | | | |215| | | | |220| | | |
|Ala|Arg|Leu|Met|Ser|Gln|Ala|Leu|Arg|Lys|Leu|Ser|His|Ser|Leu|Ser|
|225| | | | |230| | | | |235| | | | |240|
|Leu|Ser|Gln|Thr|Ile|Leu|Leu|Phe|Ile|Asn|Gln|Ile|Arg|Ala|Lys|Val|
| | | | |245| | | | |250| | | | |255| |
|Ala|Thr|Phe|Gly|Phe|Gly|Gly|Pro|Thr|Glu|Val|Thr|Ser|Gly|Gly|Asn|
| | | |260| | | | |265| | | | |270| | |
|Ala|Leu|Lys|Phe|Tyr|Ala|Ser|Val|Arg|Leu|Asn|Ile|Arg|Arg|Ile|Gly|
| | | |275| | | | |280| | | | |285| | |
|Leu|Val|Lys|Lys|Gly|Glu|Glu|Thr|Ile|Gly|Ser|Gln|Ile|Ala|Val|Lys|
| | | |290| | | | |295| | | | |300| | |
|Ile|Val|Lys|Asn|Lys|His|Ala|Pro|Pro|Phe|Lys|Thr|Ala|Gln|Phe|Glu|
|305| | | | |310| | | | |315| | | | |320|
|Leu|Glu|Phe|Gly|Lys|Gly|Ile|Cys|Arg|Ser|Ser|Glu|Leu|Phe|Glu|Leu|
| | | | |325| | | | |330| | | | |335| |
|Gly|Leu|Lys|His|Lys|Leu|Ile|Arg|Lys|Ser|Gly|Gly|Ser|Tyr|Tyr|Ser|
| | | |340| | | | |345| | | | |350| | |
|Phe|Asn|Gly|Lys|Ala|Phe|Asn|Gly|Lys|Ser|Asn|Leu|Lys|Ser|Tyr|Leu|
| | |355| | | | |360| | | | |365| | | |
|Thr|Glu|Asn|Lys|Ser|Val|Ala|Asn|Asp|Leu|Glu|Met|Glu|Leu|Lys|Arg|
| | |370| | | | |375| | | | |380| | | |
|Leu|Met|Gly|Thr|Asp|Ala|Ser|Lys|Glu|Gln|Glu|Ala|Gly|Asp|Ser|Ser|
|385| | | | |390| | | | |395| | | | |400|
|Gln|Ser|Asp|Leu|Pro|Glu|Glu|Ser|Val|Thr|Pro|Glu|Ala|Ser|Ser|Glu|

Glu Asp Leu Gly Ala Ile Ile Glu Gly
            420                 425

<210> SEQ ID NO 9
<211> LENGTH: 36
<212> TYPE: DNA
<213> ORGANISM: Artificial Sequence
<220> FEATURE:
<223> OTHER INFORMATION: Designed oligonucleotide based upon an adaptor
      used for cDNA library construction and poly (dT) to remove clones
      which have a poly(A) tail but no cDNA insert.

<400> SEQUENCE: 9
tcgacccacg cgtccgaaaa aaaaaaaaaa aaaaaa                                  36

<210> SEQ ID NO 10
<211> LENGTH: 9
<212> TYPE: PRT
<213> ORGANISM: Artificial Sequence
<220> FEATURE:
<223> OTHER INFORMATION: RecA Consensus Signature Sequence
<221> NAME/KEY: SITE
<222> LOCATION: (3)...(3)
<223> OTHER INFORMATION: Xaa = Lys or Arg
<221> NAME/KEY: SITE
<222> LOCATION: (4)...(4)
<223> OTHER INFORMATION: Xaa = Ile or Phe
<221> NAME/KEY: SITE
<222> LOCATION: (5)...(5)
<223> OTHER INFORMATION: Xaa - Phe or Tyr
<221> NAME/KEY: SITE
<222> LOCATION: (6)...(6)
<223> OTHER INFORMATION: Xaa = Ser or Thr or Ala
<221> NAME/KEY: SITE
<222> LOCATION: (7)...(7)
<223> OTHER INFORMATION: Xaa = Ser or Thr or Ala or Asp
<221> NAME/KEY: SITE
<222> LOCATION: (8)...(8)
<223> OTHER INFORMATION: Xaa = Leu or Ile or Val or Met

<400> SEQUENCE: 10

Ala Leu Xaa Xaa Xaa Xaa Xaa Xaa Arg
 1               5